United States Patent
Mack

(10) Patent No.: US 12,338,280 B2
(45) Date of Patent: Jun. 24, 2025

(54) ANTIBODIES TARGETING IL3

(71) Applicant: UNIVERSITÄTSKLINIKUM REGENSBURG, Regensburg (DE)

(72) Inventor: Matthias Mack, Regensburg (DE)

(73) Assignee: UNIVERSITÄTSKLINIKUM REGENSBURG, Regensburg (DE)

( * ) Notice: Subject to any disclaimer, the term of this patent is extended or adjusted under 35 U.S.C. 154(b) by 0 days.

(21) Appl. No.: 19/033,679

(22) Filed: Jan. 22, 2025

(65) Prior Publication Data

US 2025/0171528 A1 May 29, 2025

Related U.S. Application Data

(63) Continuation of application No. PCT/EP2023/072293, filed on Aug. 11, 2023.

(30) Foreign Application Priority Data

Aug. 11, 2022 (EP) .................................. 22190068

(51) Int. Cl.
C07K 16/24 (2006.01)

(52) U.S. Cl.
CPC ........ *C07K 16/244* (2013.01); *C07K 2317/24* (2013.01); *C07K 2317/76* (2013.01); *C07K 2317/92* (2013.01)

(58) Field of Classification Search
None
See application file for complete search history.

(56) References Cited

U.S. PATENT DOCUMENTS 11,078,266 B2 * 8/2021 Mack ................. G01N 33/6869

FOREIGN PATENT DOCUMENTS

| WO | 198804691 A1 | 6/1988 |
|----|--------------|--------|
| WO | 198911489 A1 | 11/1989 |
| WO | 200009561 A1 | 2/2000 |
| WO | 2010063488 A1 | 6/2010 |
| WO | 2013178706 A1 | 12/2013 |
| WO | 2013178707 A1 | 12/2013 |
| WO | 2015063228 A1 | 5/2015 |
| WO | 2017081218 A2 | 5/2017 |

OTHER PUBLICATIONS

Abrams and Pearce, "Development of rat anti-mouse interleukin 3 monoclonal antibodies which neutralize bioactivity in vitro," J Immunol. 1988;140(1):131-7.
International Search Report and Written Opinion received for PCT/EP2023/072293, mailed Oct. 20, 2023.
Lokker et al., "Mapping the epitopes of neutralizing anti-human IL-3 monoclonal antibodies. Implications for structure-activity relationship," J Immunol. 1991;146(3):893-8.

* cited by examiner

*Primary Examiner* — Marianne P Allen
(74) *Attorney, Agent, or Firm* — Dechert LLP; Andrew T. Wilkins; Megan E. Coyle

(57) ABSTRACT

The present disclosure relates to antibodies and antibody fragment that are specific for IL3, as well as nucleic acids encoding such antibodies and pharmaceutical compositions comprising such antibodies. The antibodies of the present invention are able to block IL-3 activity in target cells and are useful for the prevention and treatment of diseases or malfunctions which are associated with elevated levels of IL3, such as inflammatory diseases, autoimmune diseases, fibrotic diseases, hematologic malignancies and other illnesses.

18 Claims, 10 Drawing Sheets
Specification includes a Sequence Listing.

ANTIBODIES TARGETING IL3

RELATED APPLICATIONS

This application is a continuation of International Patent Application No. PCT/EP2023/072293, filed Aug. 11, 2023, which claims benefit of, and priority to EP 22190068.1, filed on Aug. 11, 2022, the entire contents of each of which are incorporated herein by reference.

SEQUENCE LISTING

The instant application contains a Sequence Listing which has been submitted electronically in XML format and is hereby incorporated by reference in its entirety. Said XML copy, created on Aug. 6, 2023, is named BHIP-C08-02-PCT sequence listing.xml and is 42,595 bytes in size.

FIELD OF THE INVENTION

The be present disclosure relates to antibodies and antibody fragment that are specific for IL3, as well as nucleic acids encoding such antibodies and pharmaceutical compositions comprising such antibodies. The antibodies of the present invention are able to block IL-3 activity in target cells and are useful for the prevention and treatment of diseases or malfunctions which are associated with elevated levels of IL3, such as inflammatory diseases, autoimmune diseases, fibrotic diseases, hematologic malignancies and other illnesses.

BACKGROUND

Interleukins belong to the large family of proteins called cytokines. Cytokines are polypeptides that influence the function of certain cells upon binding to specific cellular receptors and are divided in subclasses, i.e., interleukins, interferons, colony-stimulating factors (CSFs), lymphokines, growth factors and monokines. It is well known that cytokines play a major role in cell proliferation and, e.g., also inflammatory diseases.

Cell proliferation is a complex process wherein growth factors bind to specific receptors on the cell surface, whereupon endocytosis occurs and the complexes of cytokine and receptor are internalized causing a cellular response. Such cellular responses include specific gene transcription activities as DNA synthesis and cell replication. When tested in relatively high concentrations, most of the cytokines have several differing biological effects. Because of these effects of cytokines, there is a high interest in investigations for possible therapeutic uses of these proteins.

Interleukins are mediators of the immune system which are produced in low concentration mostly in leukocytes. They influence growth, differentiation and activity of cells of the immune system and thus belong to the immune modulators. They also take effect by binding to receptors on the surface of target cells and thus change the transcription rate of certain genes. They play an important role in the triggering of a multiplicity of cellular responses.

Interleukins are, e.g., involved in the immunological cell activation cascade and subsequent inflammatory changes. Irregular and/or abnormal inflammation is a major component and factor of a wide range of human diseases, one of which is the immunological disorder rheumatoid arthritis (RA). But also other immunological diseases are influenced by interleukins.

IL3, also designated as Multi-CSF, is a well-known member of the interleukin family. It has a growth stimulating and differentiating effect on various hematopoietic precursor cells and acts as a growth factor for mast cells and basophils. Together with IL5 and GM-CSF, IL3 belongs to the family of hematopoietic cytokines with four short alpha-helical bundles. GM-CSF and IL3 stimulate the formation of neutrophilic and eosinophilic granulocyte colonies as well as macrophages. It further stimulates the formation of mast, megakaryocyte and pure and mixed erythroid colonies (D. Metcalf, "The hematopoietic colony-stimulating factors", 1984, Elsevier, Amsterdam).

Mature IL3 consists of 133 amino acids (excluding the 19 amino acid signal sequence) and is known for its stimulation of colony formation by human hematopoietic progenitor cells and the stimulation of DNA synthesis by human acute myelogenous leukemia (AML) blasts. IL-3 binds to a unique receptor also known as CD123 antigen. The receptor belongs to the type I cytokine receptor family and is a heterodimer with a unique α-chain paired with a common β-subunit (βC or CDW 131). IL-3 binds to the unique α-receptor subunit. Signal transduction is mediated, however, by the common β-receptor subunit (βC) by the JAK2-STAT5 pathway.

Human IL-3 has two potential N-glycosylation sites at positions 15 and 70 of mature IL3. It is well established that IL3 expressed by eukaryotic cells is N-glycosylated (see e g. Biomol and Protein Expr Purif (2003) 31:34-41). The glycosylated and non-glycosylated versions of IL-3 have similar bioactivity as measured by IL3 induced proliferation of tumor cells. For murine IL-3 it was also shown that glycosylation does not affect bioactivity of IL-3 (Cytokine (1993) 5:291-7, J Biol Chem (1988), 263: 14511-7).

So far there have been no hints in the literature that glycosylation affects the ability of monoclonal antibodies to block IL3 bioactivity. The inhibitory activity of monoclonal antibodies was characterized with either *E. coli* derived IL3 (J Biol. Chem (1991) 266: 10624-31, J Immunol (1991) 146:893-8) or aglycosylated IL3 (J Biol Chem (1991) 266: 21310-7). The binding of antibodies to IL3 was tested with glycosylated and non-glycosylated IL3 and was found to be independent on the glycosylation. IL3 is mainly produced by activated CD4+ T-cells and contributes especially to growth, differentiation and survival of CD34+ hematopoietic progenitor cells. In vitro, IL3 has been observed to promote the differentiation of basophils and mast cells from bone marrow cells. It has further been observed to induce IL-6 release by murine basophils and to up-regulate MHC-11 expression and IL-1 secretion in monocyte/macrophages. Further. IL-3 supports the differentiation of monocytes into dendritic cells and osteoclasts.

Since the first detection of IL3 in a human genomic library, it has been a focus of investigations to determine its role in healthy humans as well as its possible role in the occurrence of diseases. The ability of cytokines to initiate or regulate hematopoiesis is of interest, especially as far as malfunctions or diseases of the immune system are concerned. Such disorders seem to be connected to disturbances of the hematopoietic system and it was assumed that such diseases could be treated by providing viable progenitor cells to the hematopoietic system. Triggering such progenitor cells to differentiate was considered as a means to treat the respective diseases.

Until several years ago, little was known about the role of IL3 in autoimmune diseases and especially rheumatoid arthritis (RA). RA is the most prevalent inflammatory disease of the joints. The initial disease stages often develop gradually but can also manifest themselves with an instantaneous outburst. While pain occurs predominantly in joints of the fingers or toes, also other joints can be affected. The affected joints show swelling and usually are hyperthermic. Mostly, the disease proceeds in episodes, an episode usually lasting between several weeks to months. In between episodes, generally, there is an improvement of symptoms.

The etiology of RA is not yet known. An autoimmune cause is strongly suspected with viral and bacterial causes being also discussed. A genetic influence has been reported by several authors (Arthritis Rheum (2009) 60: 661-8. Arthritis Rheum (2004); 50 3085-92). It is assumed that misdirected immune cells invade the affected joints and cause the production of pro-inflammatory cytokines. According to one theory, the balance between cytokines is disturbed in RA. It has been reported that IL1, IL6 and TNFα are present in excess in RA and are assumed to be responsible for the deleterious inflammatory processes in cartilage tissue and for the activation of osteoclasts.

The treatment of rheumatoid arthritis is still considered difficult and burdensome to the patients since medications with a high risk of adverse side effects have to be used. One way of treating the disease is to perform a symptomatic treatment, mostly using nonsteroidal anti-inflammatory drugs (NSAIDs). These drugs act as anti-inflammatory and analgetic agents and often only achieve an alleviation of pain. The drugs further interfere with a certain step in the inflammatory cascade, where prostaglandine is generated by cyclooxygenases. NSAIDs, however, do not influence the underlying inflammatory process and are thus not able to retard the joint destruction, which is the most deleterious effect of RA.

To prevent joint destruction and disease activity, a further current approach for treating RA is the use of disease-modifying anti-rheumatic drugs (DMARDs). These pharmaceuticals actually modify the disease process. Examples of DMARDs are methotrexate, the most commonly used anti-rheumatic, the effect of which is based on a reversible inhibition of the enzyme dihydrofolate reductase. Another commonly used substance for treating RA is leflunomide, which provides an effect by intervening with the pyrimidine metabolism. Both pharmaceuticals are long-acting and thus have to be administered over a longer period of time (usually 12-16 weeks) to show the desired effects. To bridge the time until DMARDs improve the disease, most patients are administered steroids.

A further approach for treating RA are "biologicals" that block cytokines like TNF, IL6. IL1 or costimulatory molecules like B7 or that deplete leukocyte subsets (e.g. B cells). Biologicals (e.g. the TNF antibody Infliximab) are mostly used for severe disease processes and after DMARDs have failed to sufficiently control disease activity. Biologicals influence a plurality of signal systems in the immune system and have a variety of serious side effects including bacterial and viral infections and a higher risk for development of neoplasia. All known treatments have severe disadvantages and side effects and, therefore, it was an object to develop new drugs for the treatment of RA which are effective, are more selectively expressed than other cytokines in patients with autoimmune disease, especially RA, and have less side effects than the currently used treatment regimes.

More recently, an involvement of IL3 in autoimmune diseases and especially in RA has been described. WO 2010/063488 describes that IL3 inhibitors can be used in treatment of early stages of rheumatoid arthritis. Although the above cited patent application mentions that no IL-3 mRNA was detected in the synovium of patients with RA and no effect of IL3 was observed on cultured fibroblasts, a genetic analysis found an association between a single nucleotide polymorphism in the IL3 promoter gene and RA. Based on this finding and also further studies which show the presence of considerably elevated levels of IL3 in RA patients, WO 2010/063488 proposes such use of inhibitors, mainly antibodies or antibody fragments, antibody variants or antibody multimers in prophylactic RA treatment, therapeutic treatment in early stages of the disease or in maintenance treatment. IL3 was also liked to other diseases, such as systemic lupus (Kidney Int (2015) 88: 1088-98), encephalitis (JCI Insight (2016) 1: e87157, myocarditis (J Exp Med (2019) 216-369-83), sepsis (Science (2015) 347: 1260-5), lung inflammation (JCI Insight (2020) 5; e133652), renal fibrosis (Kidney Int (2015) 88: 1088-98), myocardial fibrosis (J Exp Med (2019) 216: 369-83) and allograft fibrosis (J Immunol (2019) 202: 3514-23).

However, there is still a need for effective antibodies with specificity for IL3, which have a high affinity and avidity. Since the in vivo efficacy of an antibody for use in the treatment of a disease or a malfunction in a patient's body is essential, there is also an urgent need for antibodies, which are efficacious in the in vivo context. It is therefore highly desirable to provide antibodies which are able to inhibit the activity of IL3 efficiently and specifically in vivo, thus making them useful agents for treating the disease in patients having been diagnosed for elevated levels of IL3.

IL3 antibodies which meet some of these criteria are described in WO2017/081218, for example antibody P8C11 (DSM ACC3281). Antibody P8C11 is however a murine antibody. Humanization of antibody P8C11 was so far not successful. The present inventions succeeded in humanizing P8C11. The humanization process described herein is very cumbersome and involves a six-step procedure, yielding in a humanized derivative of antibody P8C11, referred to as GRT002-H16L2. Surprisingly it was found that this humanized variant not only retained the full functional activity of the parental antibody GRT002-H16L2, but also has improved biophysical properties. For example, compared the P8C11, GRT002-H16L2 shows a stability at a broader pH range and also is stable at higher temperatures.

GRT002-H16L2, as well as fragments, variants, or conjugates thereof are therefore ideally suited for clinical development for the treatment of patients requiring blocking anti-IL3 antibodies. The antibody may also be used for the detection of human IL-3 expressed in human cells.

SUMMARY OF THE INVENTION

The present disclosure relates to novel humanized antibodies and antibody fragments that are specific for human IL3. The humanized antibodies and antibody fragments are derived from a parental antibody. P8C11, which is difficult to humanize by conventional means. Surprising, the inventors not only succeeded in humanizing antibody P8C1, the humanized antibody also showed an increased stability at higher temperatures and over a broader pH range, in particular at an acidic pH.

The present disclosure relates to humanized antibodies and antibody fragments specific for human IL3 which blocks IL3 activity in TF1 cells and in human basophils.

The present disclosure relates also to humanized antibodies and antibody fragments specific for human IL3 which binds to amino acids 41-67 of human IL3 (SEQ ID NO: 1).

The present disclosure relates also to humanized antibodies and antibody fragments specific for human IL3 which do not bind to human IL-5 and human GM-CSF.

Preferred antibodies and antibody fragments of the present disclosure are of the human IgG class. Even more preferred antibodies or antibody fragment of the present disclosure are of the IgG1 class.

Preferred antibodies and antibody fragments of the present disclosure are monoclonal antibodies or antibody fragments.

The present disclosure also relates to antibodies and antibody fragments specific for human IL3 which have superior biophysical properties. This includes a high temperature stability, and a stability over a broad pH range, as compared to the parental antibody P8C11.

Preferred humanized antibodies and antibody fragments of the present disclosure comprises the HCDR1 region of SEQ ID NO: 3, the HCDR2 region of SEQ ID NO: 4, the HCDR3 region of SEQ ID NO: 5, the LCDR1 region of SEQ ID NO. 10, the LCDR2 region of SEQ ID NO. 11 and the LCDR3 region of SEQ ID NO: 12.

Preferred antibodies and antibody fragments of the present disclosure comprises a VH of SEQ ID NO: 36 and a VL of SEQ ID NO 16.

The present disclosure also relates to vectors comprising such nucleic acids or nucleic acid compositions.

The present disclosure also relates to host cells comprising such nucleic acids, nucleic acid compositions or vectors.

The antibodies and antibody fragment of the present disclosure are for use in medicine. Preferred are the antibodies and antibody fragment of the present disclosure for use in the treatment of inflammatory diseases, autoimmune diseases, fibrotic diseases, hematologic malignancies and potentially other diseases.

The present disclosure also relates to pharmaceutical composition comprising the antibodies and antibody fragments of the present disclosure and a pharmaceutically acceptable.

FIGURE LEGENDS

DEFINITIONS

Figure 1:
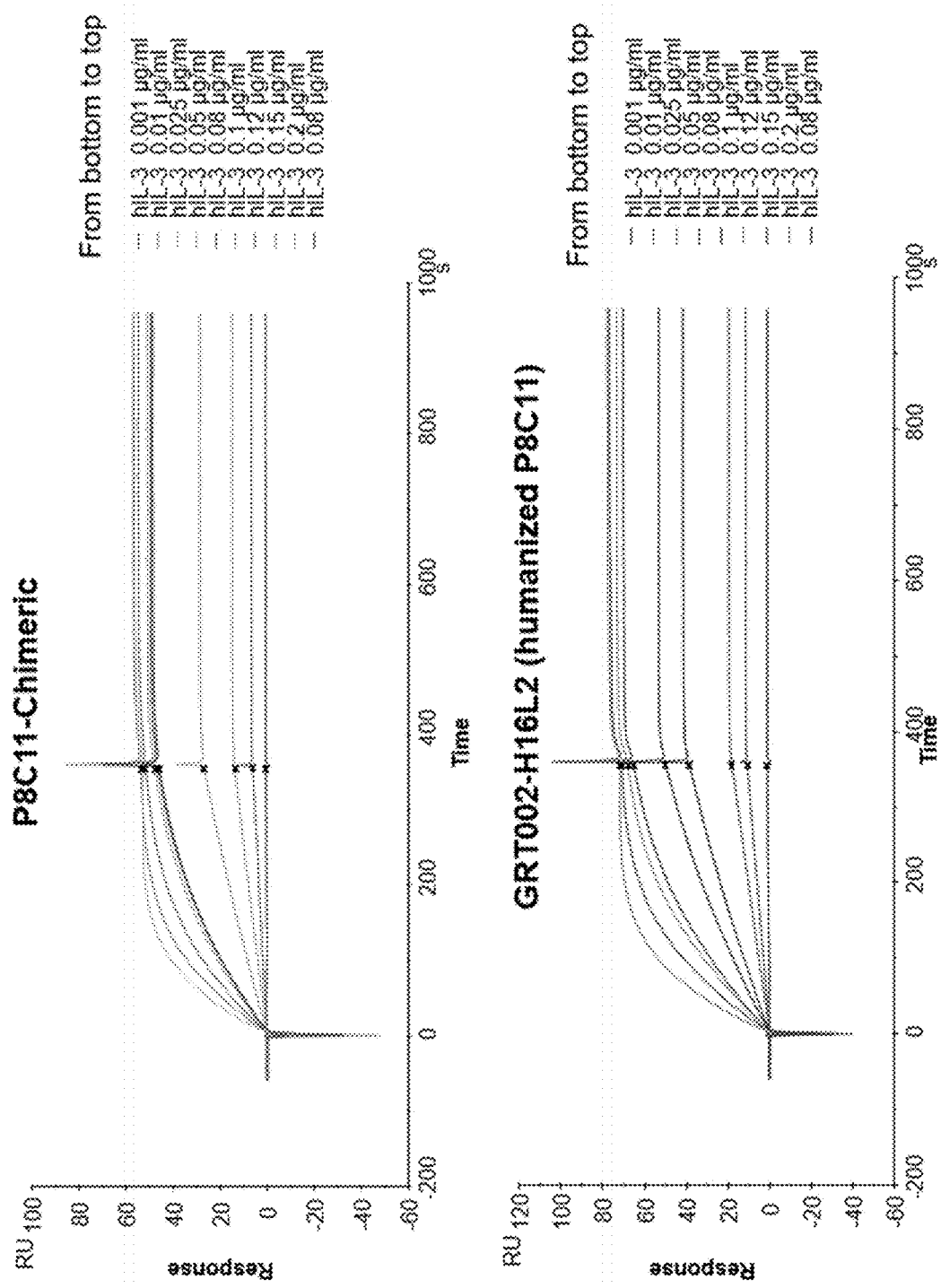
FIG. 1 shows the analysis of the binding properties of antibody GRT002-H16L2 in comparison to the parental antibody P8C11.

The disclosure pertains to antibodies, which specifically bind to IL3.

The terms "IL3" or "IL-3" refer to member of the interleukin protein family which has the following amino acid sequence (Uni Prot: P08700):

(SEQ ID No. 1)
<u>MSRLPVLLLLQLLVRPGLQ</u>APMTQTTPLKTSWVN̲CSNMIDEIITHLKQPP

LPLLDFNNLNGEDQDILMENNLRRPNLEAFNRAVKSLQN̲ASAIESILKNL

LPCLPLATAAPTRHPIHIKDGDWNEFRRKLTFYLKTLENAQAQQTTLSLA

IF

The signal sequence of IL3 is underlined in the sequence shown above. The potential N-glycosylation sites are indicated in bold and are underlined.

The term "antibody" as used herein refers to a protein comprising at least two heavy (H) chains and two light (L) chains inter-connected by disulfide bonds, which interacts with an antigen. Each heavy chain is composed of a heavy chain variable region (abbreviated herein as VH) and a heavy chain constant region. The heavy chain constant region is comprised of three domains. CH1, CH2 and CH3 Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., Igd, IgG2, IgG3, IgG4, IgA1 and IgA2) or subclass. Both the light and heavy chains are divided into regions of structural and functional homology.

The term "antibody fragment", as used herein, refers to one or more portions of an antibody that retain the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains, a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody: a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv): see e.g., Bird et al., (1988) Science 242:423-426; and Huston et al., (1988) Proc. Natl. Acad. Sci. 85:5879-5883). Such single chain antibodies are also intended to be encompassed within the term "antibody fragment" These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1 126-1 136). Antibody fragments can be grafted into scaffolds based on polypeptides such as Fibronectin type III (Fn3)(see U.S. Pat. No. 6,703,199, which describes fibronectin poly peptide monobodies). Antibody fragments can be incorporated into single chain molecules comprising a pair of tandem Fv segments (VH-CH1-VH-CH1) which, together with complementary light chain polypeptides, form a pair of antigen-binding sites (Zapata et al., (1995) Protein Eng. 8: 1057-1062; and U.S. Pat. No. 5,641,870).

The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g. Sequences of Proteins of Immunological Interest, U.S. Department of Health and Human Services (1991), eds. Kabat et al.: Lazikani et al, (1997) J. Mol. Bio. 273:927-948): Kabat et al., (1991) Sequences of Proteins of Immunological Interest, 5th edit, NIH Publication no. 91-3242 U.S. Department of Health and Human Services: Chothia et al., (1987) J. Mol. Biol. 196:901-917: Chothia et al., (1989) Nature 342:877-883; and Al-Lazikani et al., (1997) J. Mol. Biol. 273:927-948; Annals of the New York Academy of Sciences, 764, 47-49 (1995): Nucleic Acids Research, 25, 206-211 (1997).

A "human antibody" or "human antibody fragment", as used herein, is an antibody and antibody fragment having variable regions in which both the framework and CDR regions are from sequences of human origin. Human antibodies can also be isolated from synthetic libraries or from transgenic mice (e.g. Xenomouse) provided the respective system yield in antibodies having variable regions in which both the framework and CDR regions are derived from sequences of human origin. Furthermore, if the antibody contains a constant region, the constant region also is derived from such sequences. Human origin includes, e.g., human germline sequences, or mutated versions of human germline sequences or antibody containing consensus framework sequences derived from human framework sequences analysis, for example, as described in Knappik et al., (2000) J Mol Biol 296:57-86).

A "humanized antibody" or "humanized antibody fragment" is defined herein as an antibody molecule, which has constant antibody regions derived from sequences of human origin and the variable antibody regions or parts thereof or only the CDRs are derived from another species. For example, a humanized antibody can be CDR-grafted, wherein the CDRs of the variable domain are from a non-human origin, while one or more frameworks of the variable domain are of human origin and the constant domain (if any) is of human origin.

The term "chimeric antibody" or "chimeric antibody fragment" is defined herein as an antibody molecule, which has constant antibody regions derived from, or corresponding to, sequences found in one species and variable antibody regions derived from another species. Preferably, the constant antibody regions are derived from, or corresponding to, sequences found in humans, and the variable antibody regions (e.g. VH. VL, CDR or FR regions) are derived from sequences found in a non-human animal, e.g. a mouse, rat, rabbit or hamster.

The term "isolated antibody" refers to an antibody or antibody fragment that is substantially free of other antibodies or antibody fragments having different antigenic specificities. Moreover, an isolated antibody or antibody fragment may be substantially free of other cellular material and/or chemicals. Thus, in some aspects, antibodies provided are isolated antibodies, which have been separated from antibodies with a different specificity. An isolated antibody may be a monoclonal antibody. An isolated antibody may be a recombinant monoclonal antibody. An isolated antibody that specifically binds to an epitope, isoform or variant of a target may, however, have cross-reactivity to other related antigens, e.g., from other species (e.g., species homologs).

The term "recombinant antibody", as used herein, includes all antibodies that are prepared, expressed, created or segregated by means not existing in nature. For example, antibodies isolated from a host cell transformed to express the antibody, antibodies selected and isolated from a recombinant, combinatorial human antibody library, and antibodies prepared, expressed, created or isolated by any other means that involve splicing of all or a portion of a human immunoglobulin gene, sequences to other DNA sequences or antibodies isolated from an animal (e.g., a mouse) that is transgenic or transchromosomal for human immunoglobulin genes or a hybridoma prepared therefrom. Preferably, such recombinant antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. A recombinant antibody may be a monoclonal antibody. In an embodiment, the antibodies and antibody fragment disclosed herein are isolated from the HuCAL library (Rothe et al, J. Mol. Biol. (2008) 376, 1 182-1200).

As used herein, an antibody "binds specifically to", "specifically binds to", is "specific to/for" or "specifically recognizes" an antigen, such as human IL3, if such antibody is able to discriminate between such antigen and one or more reference antigen(s), since binding specificity is not an absolute, but a relative property. For example, a standard ELISA assay or standard flow cytometry assay can be carried out. The scoring may be carried out by standard color development (e.g. secondary antibody with horseradish peroxide and tetramethyl benzidine with hydrogen peroxide) or by binding of a secondary antibody labeled with PE or another dye or marker. The reaction in certain wells is scored by the optical density (OD), for example, at 450 nm or by mean fluorescence intensity (MFI) in flow cytometry. Typical background (=negative reaction) may be 0.1 OD; typical positive reaction may be 1 OD. Background and positive reaction MFI are highly dependent on instrument settings. The difference positive/negative can be more than 10-fold. Typically, determination of binding specificity is performed by using not a single reference antigen, but a set of about three to five unrelated antigens, such as milk powder, BSA, transferrin or the like. For flow cytometry various antigen-negative cells can be used. An antibody that specifically binds to an antigen may however have cross-reactivity to the respective orthologous antigen from other species (e.g., species homologs). In certain embodiments such cross-reactivity to an orthologous antigen is even preferred.

As used herein, an antibody has "cross-reactivity" or is "cross-reactive" if it binds to the orthologous antigen from other species. For example, an antibody is cross-reactive if it binds to human IL3 and to marmoset IL3.

As used herein, the term "affinity" refers to the strength of interaction between the polypeptide and its target at a single site. Within each site, the binding region of the polypeptide interacts through weak non-covalent forces with its target at numerous sites: the more interactions, the stronger the affinity.

The term "epitope" includes any proteinaceous region which is specifically recognized by an antibody or antibody fragment thereof or otherwise interacts with a molecule. Generally, epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

The term "domain" or "protein domain" refers to a region of a protein's polypeptide chain that forms a functional unit and/or independently forms a three-dimensional structure.

"Compositions" of the present disclosure may be used for therapeutic or prophylactic applications. The present disclosure, therefore, includes a pharmaceutical composition containing an antibody or antibody fragment as disclosed herein and a pharmaceutically acceptable carrier or excipient therefore. In a related aspect, the present disclosure provides a method for treating inflammatory diseases, autoimmune diseases, fibrotic diseases, hematologic malignancies and potentially other diseases. Such method contains the steps of administering to a subject in need thereof an effective amount of the pharmaceutical composition that contains an antibody or antibody fragment as described herein.

The present disclosure provides therapeutic methods comprising the administration of a therapeutically effective amount of an antibody or antibody fragment as disclosed herein to a subject in need of such treatment. A "therapeutically effective amount" or "effective amount", as used herein, refers to the amount of a IL3 antibody necessary to elicit the desired biological response. In accordance with the subject disclosure, the therapeutic effective amount is the amount of a IL3 antibody necessary to treat and/or prevent a disease.

"Administered" or "administration" includes but is not limited to delivery of a drug by an injectable form, such as, for example, an intravenous, intramuscular, intradermal or subcutaneous route or mucosal route, for example, as a nasal spray or aerosol for inhalation or as an ingestible solution, capsule or tablet. Preferably, the administration is by an injectable form.

As used herein, "treatment", "treat" or "treating" and the like refers to clinical intervention in an attempt to alter the natural course of a disease in the subject being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or antibody fragments according to the preset disclosure are used to delay development of a disease or to slow the progression of a disease.

"Preventing" or "prevention" refers to a reduction in risk of acquiring or developing a disease (i.e. causing at least one of the clinical symptoms of the disease not to develop in a subject that may be exposed to a disease-causing agent, or predisposed to the disease in advance of disease onset). "Prevention" also refers to methods which aim to prevent the onset of a disease or its symptoms or which delay the onset of a disease or its symptoms.

"Subject" or "species" or as used in this context refers to any mammal, including rodents, such as mouse ormrat, and primates, such as cynomolgus monkey (*Macaca fascicularis*), Marmoset monkey (*Callithrix jacchus*), rhesus monkey (*Macaca mulatta*) or humans (*Homo sapiens*). Preferably, the subject is a primate, most preferably a human.

The term "effector function" refers to those biological activities attributable to the Fc region of an antibody, which vary with the antibody isotype. Non-limiting examples of antibody effector functions include C1q binding and complement dependent cytotoxicity (CDC), Fc receptor binding and antibody-dependent cell-mediated cytotoxicity (ADCC) and/or antibody-dependent cellular phagocytosis (ADCP); down regulation of cell surface receptors (e.g. B cell receptor); and direct cell activation or direct cell inhibition.

"Antibody-dependent cell-mediated cytotoxicity" or "ADCC" refers to a form of cytotoxicity in which antibodies bound onto Fc receptors (FcRs) present on certain cytotoxic cells (e g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes/macrophages express FcγRI, FcγRII, and FcγRIII.

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass) of the present disclosure, which are bound to their cognate antigen.

"Antibody-dependent cellular phagocytosis" or "ADCP" refers to a mechanism of elimination of antibody-coated target cells by internalization by phagocytic cells, such as macrophages or dendritic cells.

Throughout this specification, unless the context requires otherwise, the words "comprise", "have" and "include" and their respective variations such as "comprises", "comprising", "has", "having" "includes" and "including" will be understood to imply the inclusion of a stated element or integer or group of elements or integers but not the exclusion of any other element or integer or group of elements or integers.

The terms "engineered" or "modified" as used herein includes manipulation of nucleic acids or polypeptides by synthetic means (e.g. by recombinant techniques, in vitro peptide synthesis, by enzymatic or chemical coupling of peptides or some combination of these techniques). Preferably, the antibodies or antibody fragments according to the present disclosure are engineered or modified to improve one or more properties, such as antigen binding, stability, half-life, effector function, immunogenicity, safety and the like.

"Variant" as used herein refers to a polypeptide that differs from a reference polypeptide by one or more modifications for example amino acid substitutions, insertions or deletions. Variant polypeptides typically retain most of the properties of the reference polypeptide, e g. binding to the target antigen, but introduce a novel, additional feature or property, e.g. the variant polypeptide has a higher affinity to the target antigen compared to the reference polypeptide or the variant polypeptide is a humanized version of the reference polypeptide.

The term "amino acid mutation" as used herein is meant to encompass amino acid substitutions, deletions, insertions, and modifications. Any combination of substitution, deletion, insertion, and modification can be made as long as the final construct possesses the desired characteristics, e.g., reduced binding to an Fc receptor. Amino acid sequence deletions and insertions include N- and/or C-terminal deletions and insertions of amino acid residues. Particular amino acid mutations are amino acid substitutions. Amino acid substitutions include replacement by non-naturally occurring amino acids or by naturally occurring amino acid derivatives of the twenty standard amino acids. Amino acid mutations can be generated using genetic or chemical methods well known in the art. Genetic methods may include site-directed mutagenesis, βCR, gene synthesis and the like. It is contemplated that methods of altering the side chain group of an amino acid residue by methods other than genetic engineering, such as chemical modification, may also be useful. Various designations may be used herein to indicate the same amino acid mutation. For example, a substitution from glyince at position 327 of the Fc region to alanine can be indicated as 327, G327, G327A, or Glyv327Ala.

The term "EC50" as used herein, refers to the concentration of an antibody or antibody fragment, which induces a response in an assay half way between the baseline and maximum. It therefore represents the antibody or ligand concentration at which 50% of the maximal effect is observed.

The terms "inhibition" or "inhibit" or "reduction" or "reduce" or "neutralization" or "neutralize" refer to a decrease or cessation of any phenotypic characteristic (such as binding or a biological activity or function) or to the decrease or cessation in the incidence, degree, or likelihood of that characteristic. "Inhibition", "reduction" or "neutralization" needs not to be complete as long as it is detectable using an appropriate assay. In some embodiments, by "reduce" or "inhibit" or "neutralize" is meant the ability to cause a decrease of 20% or greater. In another embodiment, by "reduce" or "inhibit" or "neutralize" is meant the ability to cause a decrease of 50% or greater. In yet another embodiment, by "reduce" or "inhibit" or "neutralize" is meant the ability to cause an overall decrease of 75%, 85%, 90%, 95%, or greater.

The term "antagonistic" antibody as used herein refers to an antibody or antibody fragment that interacts with an antigen and partially or fully inhibits or neutralizes a biological activity or function or any other phenotypic characteristic of a target antigen.

A "wild-type" protein is a version or variant of the protein as it is found in nature. An amino acid sequence of a wildtype protein, e.g., a Fc region of an human IgG1 antibody, is the amino acid sequence of the protein as it occurs in nature. Due to allotypic differences, there can be more than one amino acid sequence for a wildtype protein. For example, there are several allotypes of naturally occurring human IGg1 heavy chain constant regions (see, e.g., Jeffries et al. (2009) mAbs 1:1).

The "Fc region" is used to define the C-terminal region of an immunoglobulin heavy chain. The Fc region of an immunoglobulin generally comprises two constant domains, a CH2 domain and a CH3 domain. Although the boundaries of the Fc region of an IgG heavy chain might vary slightly, the human IgG heavy chain Fc region is usually defined to extend from Cys226, or from Pro230, to the C-terminus of the heavy chain. However, the C-terminal lysine (Lys447) of the Fc region may or may not be present. Unless otherwise specified herein, numbering of amino acid residues in the Fc region is according to the EU numbering system, also called the EU index, as described in Kabat et al., Sequences of Proteins of Immunological Interest, 5th Ed. Public Health Service, National Institutes of Health. Bethesda, MD, 1991.

Embodiments of the Invention

In the prior art, the efficacy of potential IL3 specific antibodies was tested on leukemia cell lines or TF1 cells. TF1 is a model human erythroblast cell line, which has been established by T. Kitamura in 1987 from bone marrow of a 35 year old male Japanese suffering from severe pancytopenia. Growth of TF1 cells is completely dependent on the presence of IL-3 or GM-CSF. Thus, a test based on the cell proliferation of TF1 cells can be used to determine blocking of the IL-3 activity which in turn leads to a decrease or even a complete inhibition of the growth of TF1 cells.

For using an antibody in the treatment of humans, the capability of blocking IL-3 activity should also be assayed in a model which is not as remote from the in vivo context, as is the TF1 cell line model. Therefore, the inventors tested the anti-IL3 antibodies of the present disclosure with primary human cells obtained from a patient to be treated with the anti-IL3 antibodies or from healthy subjects as controls. Primary cells and use of IL3 produced by primary human cells are superior to a cell line model.

The glycosylation status is depending on the type of cell producing human IL-3. If human IL-3 is produced recombinantly by *E. coli* cells, the resulting human IL-3 will not be glycosylated. If human IL-3 is produced by insect cells, the resulting human IL-3 will be weakly glycosylated. If IL-3 is produced by human cells, such as HEK cells, the resulting human IL-3 will be more strongly glycosylated.

Primary cells used to determine the efficiency of the anti-IL3 antibodies of the present disclosure are primary human blood cells, preferably obtained from a patient suffering from rheumatoid arthritis (RA). The primary human blood cells can also be obtained from a healthy subject, and can be used as a control. For testing a blood sample can be treated with heparin, citrate, or EDTA as anti-coagulant as is known in the art. Preferably, EDTA is added to the blood sample as anti-coagulant. This kind of blood sample is also referred to as "EDTA blood".

Primary human blood cells contain basophil granulocytes, also termed "basophils", which can be detected with known methods, such as flow cytometry using labelled antibodies, such as combinations of fluorescently labelled antibodies directed against basophil expressed cell markers, such as CD11b, CD123, CCR3, and CD203c. Capability to block human IL3 activity can for example be tested by assaying IL3 induced upregulation of CD203c in basophil granulocytes (Int J Immunopathol Pharmacol (2007) 20:267-78). IL-3 also induces upregulation of CD11b and downregulation of CD131 in basophils. Furthermore, human IL3 induces upregulation of HLA-DR and downmodulation of CD131 in plasmocytoid dendritic cells (pDC), which are also comprised in a blood sample comprising primary human blood cells, pDCs can be detected as is known in the art, such as by flow cytometry using combinations of fluorescently labelled antibodies directed against dendritic cell expressed cell markers, such as HLA-DR, CD123, and CD4. In addition. IL3 induced downregulation of CD131 can be quantified on CD14+CD16+ monocytes, CD14++ monocytes, and eosinophils. Therefore, the capability of anti-IL-3 antibodies to efficiently block hIL-3 activity can be assayed by known tests, such as by quantifying the upregulation of CD11b and CD203c in basophils, or of HLA-DR in pDCs, or the downregulation of CD131 in various cell types including basophils, pDC, monocytes or eosinophils. Basophils are the preferred cell type to quantify the bioactivity of IL3 in a human sample, because basophils strongly react to IL-3 and show little reactivity to closely related cytokines such as IL-5 and GM-CSF.

Polypeptides

In an embodiment, the present disclosure relates to a humanized antibody or antibody fragment specific for human IL3, wherein said antibody or antibody fragment comprises the HCDR1 region of SEQ ID NO: 3, the HCDR2 region of SEQ ID NO: 4, the HCDR3 region of SEQ ID NO: 5, the LCDR1 region of SEQ ID NO. 10, the LCDR2 region of SEQ ID NO: 11 and the LCDR3 region of SEQ ID NO: 12.

In an embodiment, the present disclosure relates to a humanized antibody or antibody fragment specific for human IL3, wherein said antibody or antibody fragment comprises the HCDR1 region of SEQ ID NO: 3, the HCDR2 region of SEQ ID NO: 4, the HCDR3 region of SEQ ID NO. 5, the LCDR1 region of SEQ ID NO: 10, the LCDR2 region of SEQ ID NO. 11 and the LCDR3 region of SEQ ID NO: 12, as defined by Kabat.

In an embodiment, the present disclosure relates to a humanized antibody or antibody fragment specific for human IL3, wherein said antibody or antibody fragment comprises the HCDR1 region of SEQ ID NO: 6, the HCDR2 region of SEQ ID NO: 7, the HCDR3 region of SEQ ID NO: 8, the LCDR1 region of SEQ ID NO: 13, the LCDR2 region of KAS and the LCDR3 region of SEQ ID NO: 12, as defined by IMGT.

In an embodiment, the present disclosure relates to a humanized antibody or antibody fragment specific for human IL3, wherein said antibody or antibody fragment comprises a VH of SEQ ID NO: 36 and a VL of SEQ ID NO 16.

In an embodiment of the present disclosure, the humanized antibody or antibody fragment is a monoclonal antibody or antibody fragment.

In an embodiment of the present disclosure, the humanized antibody or antibody fragment is recombinant antibody or antibody fragment.

In an embodiment of the present disclosure, the humanized antibody or antibody fragment is of the IgG isotype.

In an embodiment of the present disclosure, the humanized antibody or antibody fragment is of the IgG1 class.

In an embodiment, the present disclosure relates to a humanized antibody or antibody fragment specific for human IL3, wherein said antibody comprises a heavy chain of SEQ ID NO 44 and a light chain of SEQ ID NO 45.

In an embodiment, the present disclosure relates to a humanized antibody or antibody fragment specific for human IL3, wherein said antibody has a heavy chain of SEQ ID NO: 44 and a light chain of SEQ ID NO 45.

In an embodiment of the present disclosure, the humanized antibody or antibody fragment is specific for a polypeptide encoded by the amino acid sequence of SEQ ID NO: 1.

In an embodiment of the present disclosure, the humanized antibody or antibody fragment is specific for a polypeptide comprising the amino acid sequence of SEQ ID NO: 1.

In another embodiment of the present disclosure, the humanized antibody or antibody fragment binds to binds to amino acids 41-67 of human IL3 (SEQ ID NO: 1). In another embodiment of the present disclosure, the humanized antibody or antibody fragment binds to binds to amino acids 22-48 of mature human IL3. In another embodiment of the present disclosure, the humanized antibody or antibody fragment binds to binds to a peptide stretch consisting of the amino acids of SEQ ID NO: 37 of human IL3. In another embodiment of the present disclosure, the humanized antibody or antibody fragment binds to binds to a peptide comprising the amino acids of SEQ ID NO: 37 In another embodiment of the present disclosure, the humanized antibody or antibody fragment binds to binds to a peptide consisting of the amino acids of SEQ ID NO: 37. In another embodiment of the present disclosure, the humanized antibody or antibody fragment binds to binds to a peptide comprising the amino acids of SEQ ID NO: 38. In another embodiment of the present disclosure, the humanized antibody or antibody fragment binds to binds to a peptide consisting of the amino acids of SEQ ID NO: 38. In another embodiment of the present disclosure, the humanized antibody or antibody fragment binds to binds to a peptide comprising the amino acids of SEQ ID NO. 39. In another embodiment of the present disclosure, the humanized antibody or antibody fragment binds to binds to a peptide consisting of the amino acids of SEQ ID NO: 39. In preferred embodiments, said antibody or antibody fragment comprises a VII of SEQ ID NO. 36 and a VL of SEQ ID NO 16.

In another embodiment of the present disclosure, the humanized antibody or antibody fragment specific for human IL3 is not cross-reactive with IL3 from other species. In certain embodiments of the present disclosure, the humanized antibody or antibody fragment specific for human IL3 is not cross-reactive with mouse IL3 or rat IL3. In certain embodiments of the present disclosure, the humanized antibody or antibody fragment specific for human IL3 is not cross-reactive with rat IL3. In certain embodiments of the present disclosure, the humanized antibody or antibody fragment specific for human IL3 is not cross-reactive with mouse IL3 In preferred embodiments, said antibody or antibody fragment comprises a VH of SEQ ID NO: 36 and a VL of SEQ ID NO: 16.

To determine the usefulness of the obtained monoclonal antibodies for diagnostic assays, it is important to be able to exclude cross-reactivity with closely related cytokines which are also present in blood, plasma, serum or other body fluids of patients. IL5 (UniProt: P05113) and GM-CSF (UniProt: P04141) are two such closely related cytokines. Therefore, in another embodiment of the present disclosure, the humanized antibody or antibody fragment specific for human IL3 is not cross-reactive with human IL5 or human GM-CSF. In certain embodiments of the present disclosure, the humanized antibody or antibody fragment specific for human IL3 is not cross-reactive with human IL5. In certain embodiments of the present disclosure, the humanized antibody or antibody fragment specific for human IL3 is not cross-reactive with human GM-CSF. In preferred embodiments, said antibody or antibody fragment comprises a VH of SEQ ID NO 36 and a VL of SEQ ID NO 16.

In another embodiment of the present disclosure, the humanized antibody or antibody fragment specific for human IL3 blocks IL3 activity in TF1 cells and in human basophils. In certain embodiments of the present disclosure, the humanized antibody or antibody fragment specific for human IL3 blocks IL3 activity in TF1 cells. In certain embodiments of the present disclosure, the humanized antibody or antibody fragment specific for human IL3 blocks IL3 activity in human basophils. In certain embodiments of the present disclosure, the humanized antibody or antibody fragment specific for human IL3 blocks IL3 activity in TF1 cells at least to the same degree as an antibody or antibody fragment comprising the VH of SEQ ID NO: 2 and the VL of SEQ ID NO 9. In certain embodiments of the present disclosure, the humanized antibody or antibody fragment specific for human IL3 blocks IL3 activity in human basophils at least to the same degree as an antibody or antibody fragment comprising the VH of SEQ ID NO: 2 and the VL of SEQ ID NO 9. In preferred embodiments, said antibody or antibody fragment comprises a VH of SEQ ID NO. 36 and a VL of SEQ ID NO 16.

In another embodiment of the present disclosure, the humanized antibody or antibody fragment specific for human IL3 has an increased temperature stability. In certain embodiment of the present disclosure, the humanized antibody or antibody fragment specific for human IL3 has an increased temperature stability at 75° C. In certain embodiment of the present disclosure, the humanized antibody or antibody fragment specific for human IL3 has an increased temperature stability at 75° C., compared to an antibody or antibody fragment comprising the VH of SEQ ID NO: 2 and the VL of SEQ ID NO 9. In preferred embodiments, said antibody or antibody fragment comprises a VH of SEQ ID NO: 36 and a VL of SEQ ID NO 16.

In another embodiment of the present disclosure, the humanized antibody or antibody fragment specific for human IL3 has an increased pH stability. In certain embodiment of the present disclosure, the humanized antibody or antibody fragment specific for human IL3 has an increased stability at pH2. In certain embodiment of the present disclosure, the humanized antibody or antibody fragment specific for human IL3 has an increased stability at pH2 compared to an antibody or antibody fragment comprising the VH of SEQ ID NO. 2 and the VL of SEQ ID NO 9. In preferred embodiments, said antibody or antibody fragment comprises a VH of SEQ ID NO: 36 and a VL of SEQ ID NO 16.

Nucleic Acids

In an embodiment, the present disclosure relates to a nucleic acid composition comprising a nucleic acid sequence or a plurality of nucleic acid sequences encoding a humanized antibody or antibody fragment specific for human IL3, wherein said antibody or antibody fragment comprises the HCDR1 region of SEQ ID NO: 3, the HCDR2 region of SEQ ID NO: 4, the HCDR3 region of SEQ ID NO 5, the LCDR1 region of SEQ ID NO. 10, the LCDR2 region of SEQ ID NO: 1 and the LCDR3 region of SEQ ID NO: 12.

In an embodiment, the present disclosure relates to a nucleic acid composition comprising a nucleic acid sequence or a plurality of nucleic acid sequences encoding a humanized antibody or antibody fragment specific for human IL3, wherein said antibody or antibody fragment contains the HCDR1 region of SEQ ID NO: 3, the HCDR2 region of SEQ ID NO: 4, the HCDR3 region of SEQ ID NO: 5, the LCDR1 region of SEQ ID NO: 10, the LCDR2 region of SEQ ID NO: 11 and the LCDR3 region of SEQ ID NO 12.

In an embodiment, the present disclosure relates to a nucleic acid composition comprising a nucleic acid sequence or a plurality of nucleic acid sequences encoding a humanized antibody or antibody fragment specific for human IL3, wherein said antibody or antibody fragment comprises the HCDR1 region of SEQ ID NO: 3, the HCDR2 region of SEQ ID NO: 4, the HCDR3 region of SEQ ID NO 5, the LCDR1 region of SEQ ID NO. 10, the LCDR2 region of SEQ ID NO: 11 and the LCDR3 region of SEQ ID NO: 12, as defined by Kabat.

In an embodiment, the present disclosure relates to a nucleic acid composition comprising a nucleic acid sequence or a plurality of nucleic acid sequences encoding a humanized antibody or antibody fragment specific for human IL3, w % herein said antibody or antibody fragment contains the HCDR1 region of SEQ ID NO: 3, the HCDR2 region of SEQ ID NO: 4, the HCDR3 region of SEQ ID NO: 5, the LCDR1 region of SEQ ID NO: 10, the LCDR2 region of SEQ ID NO: 11 and the LCDR3 region of SEQ ID NO: 12, as defined by Kabat.

In an embodiment, the present disclosure relates to a nucleic acid composition comprising a nucleic acid sequence or a plurality of nucleic acid sequences encoding a humanized antibody or antibody fragment specific for human IL3, wherein said antibody or antibody fragment comprises a VH of SEQ ID NO: 36 and a VL of SEQ ID NO 16.

In an embodiment, the present disclosure relates to a nucleic acid composition comprising a nucleic acid sequence or a plurality of nucleic acid sequences encoding a humanized antibody or antibody fragment specific for human IL3, w % herein said antibody or antibody fragment contains a VH of SEQ ID NO: 36 and a VL of SEQ ID NO 16.

In an embodiment, said nucleic acid composition and/or said nucleic acid sequence and/or plurality of nucleic acid sequences are isolated Vectors In an embodiment, the present disclosure provides a vector composition comprising a vector or a plurality of vectors comprising a nucleic acid composition comprising a nucleic acid sequence or a plurality of nucleic acid sequences encoding a humanized antibody or antibody fragment specific for human IL3 according to the present disclosure.

In an embodiment, the present disclosure provides a vector composition comprising a vector or a plurality of vectors comprising a nucleic acid composition comprising a nucleic acid sequence or a plurality of nucleic acid sequences encoding any one of the humanized antibodies or antibody fragments specific for human IL3 disclosed herein.

In an embodiment, said vector composition and/or vector and/or plurality of vectors are isolated.

Host Cells

In an embodiment, the present disclosure provides a host cell comprising a vector composition comprising a vector or a plurality of vectors comprising a nucleic acid composition comprising a nucleic acid sequence or a plurality of nucleic acid sequences encoding a humanized antibody or antibody fragment specific for human IL3 according to the present disclosure.

In an embodiment, the present disclosure refers to a host cell comprising a vector composition comprising a vector or a plurality of vectors comprising a nucleic acid composition comprising a nucleic acid sequence or a plurality of nucleic acid sequences encoding a humanized antibody or antibody fragment specific for IL3, wherein said antibody or antibody fragment comprises a VH of SEQ ID NO 36 and a VL of SEQ ID NO 16.

In an embodiment, the host cell according to the present disclosure is able to express the humanized antibody or antibody fragment specific for human IL3 encoded by the vector composition or the nucleic acid composition.

In a further embodiment, the host cell is an isolated host cell. In a further embodiment, said host cell is a mammalian cell. In an embodiment, said mammalian cell is a human cell. In another embodiment, said mammalian cell is a CHO cell. In an embodiment, said cell is a HEK cell. In another embodiment, said cell is a PERC 6 cell. In an embodiment, said cell is a HKB11 cell.

The skilled man will realize that the nucleic acid sequence or the plurality of nucleic acid sequences encoding the heavy and/or light chain of an antibody or antibody fragment of the present disclosure can be cloned into different vectors or into the same vector.

The vectors can be introduced into the appropriate host cells such as prokaryotic (e.g., bacterial) or eukaryotic (e.g., yeast or mammalian) cells by methods well known in the art (see e.g., "Current Protocol in Molecular Biology". Ausubel et al. (eds.), Greene Publishing Assoc and John Wiley Interscience, New York, 1989 and 1992). Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the nucleic acid sequence encoding the desired protein is transcribed into RNA in the host cell transformed by a vector containing this expression construction. The coding sequence may or may not contain a signal peptide or leader sequence. Upon expression in host cells, the antibodies or antibody fragments of the present disclosure are obtained. These steps can be achieved in different ways, as will be known by the person skilled in the art. In general, such steps typically include transforming or transfecting a suitable host cell with a nucleic acid composition or vector composition or an infectious particle, which encodes the antibody, or antibody fragments. Further, such steps typically include culturing said host cells under conditions suitable for the proliferation (multiplication, growth) of said host cells and a culturing step wider conditions suitable for the production (expression, synthesis) of the encoded antibody or antibody fragment. The culturing of host cells under conditions suitable for proliferation or expression is typically accomplished in the presence of media comprising components suitable for cell growth or induction of expression. In particular, embodiments, the methods for the production of the antibodies or antibody fragments of the present disclosure further comprise the step of isolating and purifying the produced antibody or antibody fragment from the host cells or medium. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art. The antibody or antibody fragment of the present disclosure can then be purified by a number of techniques as known to the person skilled in the art.

In an embodiment, the present disclosure refers to a method of producing a humanized antibody or antibody fragment specific for human IL3, wherein said antibody or antibody fragment comprises a VH of SEQ ID NO: 36 and a VL of SEQ ID NO 16. In an embodiment, a method of producing a humanized antibody or antibody fragment according to the present disclosure is provided, wherein the method comprises culturing a host cell comprising a vector composition comprising a vector or a plurality of vectors comprising a nucleic acid composition comprising a nucleic acid sequence or a plurality of nucleic acid sequences encoding an antibody or antibody fragment according to the present disclosure, under conditions suitable for expression of the antibody or antibody fragment, and isolating the antibody or antibody fragment from the host cell or host cell culture medium. An antibody or antibody fragment isolated as described herein may be purified techniques know in the art, such as high performance liquid chromatography (HPLC), ion exchange chromatography, gel electrophoresis, affinity chromatography, size exclusion chromatography, and the like. The conditions used to purify a particular antibody or antibody fragment will depend, in part, on factors such as net charge, hydrophobicity, hydrophilicity etc., and will be apparent to those having skill in the art. For affinity chromatography purification an antibody, ligand, receptor or antigen can be used to which the antibody or antibody fragment binds. For example, for affinity chromatography purification of antibody or antibody fragment according to the present disclosure, a matrix with protein A or protein G may be used. The purity of an antibody or antibody fragment can be determined by any of a variety of well-known analytical methods including gel electrophoresis, high-pressure liquid chromatography, and the like.

Effector Function

The Fc region of an immunoglobulin generally confers to the favorable pharmacokinetic properties of antibodies, such as prolonged half-life in serum and to the ability to induce effector function via binding to Fc receptors expressed on cells. On the other hand, binding to Fc receptors might also results in an undesirable activation of certain cell surface receptors leading to unwanted cytokine release and severe side effects upon systemic administration.

Accordingly, for certain therapeutic situations, it is desirable to reduce or abolish the normal binding of the wild-type Fc region of an antibody, such as of an wild-type IgG Fc region to one or more or all of Fc receptors and/or binding to a complement component, such as C1 q in order to reduce or abolish the ability of the antibody to induce effector function. For instance, it may be desirable to reduce or abolish the binding of the Fc region of an antibody to one or more or all of the Fcy receptors, such as: FcyRI, FcyRIIa, FcyRIIb, FcyRIIIa. Effector function can include, but is not limited to, one or more of the following: complement dependent cytotoxicity (CDC), antibody-dependent cell-mediated cytotoxicity (ADCC), antibody-dependent cellular phagocytosis (ADCP), cytokine secretion, immune complex-mediated antigen uptake by antigen-presenting cells, binding to NK cells, binding to macrophages, binding to monocytes, binding to polymorphonuclear cells, direct signaling inducing apoptosis, crosslinking of target-bound antibodies, dendritic cell maturation, or T cell priming.

A reduced or abolished binding of an Fc region to an Fc receptor and/or to C1 q is typically achieved by mutating a wild-type Fc region, such as of an IgG1 Fc region, more particular a human IgG1 Fc region, resulting in a variant or engineered Fc region of said wild-type Fc region, e.g. a variant human IgG1 Fc region. Substitutions that result in reduced binding can be useful. For reducing or abolishing the binding properties of an Fc region to an Fc receptor, non-conservative amino acid substitutions, i.e. replacing one amino acid with another amino acid having different structural and/or chemical properties, are preferred.

Accordingly, in an embodiment, the isolated antibody or antibody fragment specific for human IL3 according to the present disclosure comprises a variant Fc region having a reduced or abolished binding to an Fc receptor and/or to C1q when compared to the wild-type Fc region. In one such embodiment, the isolated antibody or antibody fragment according to the present disclosure comprises a variant Fc region that reduces or abolishes the ability of the antibody to induce effector function. In a further embodiment, the isolated antibody or antibody fragment according to the present disclosure does not substantially induce effector function.

In certain embodiments, the effector function is one or more selected from the group consisting of CDC, ADCC and ADCP. In an embodiment, the effector function is ADCC. In an embodiment, the effector function is CDC. In an embodiment, the effector function is ADCP. In an embodiment, the isolated antibody or antibody fragment according to the present disclosure does not substantially induce ADCC and/or CDC and/or ADCP. In an embodiment, the isolated antibody or antibody fragment according to the present disclosure does not induce ADCC or ADCP in vitro.

In an embodiment, the variant Fc region of the humanized antibody or antibody fragment according to the present disclosure comprises one or more amino acid substitutions that reduce or abolish the binding of the variant Fc region to one or more Fc receptors and/or to C1q when compared to the wild-type Fc region. In an embodiment, the variant Fc region of the humanized antibody or antibody fragment according to the present disclosure comprises one or more amino acid substitutions that reduce or abolish the ability of the antibody to induce effector function when compared to the wild-type Fc region. In a particular embodiment, the one or more amino acid substitutions may reduce the binding affinity of the variant Fc region for one or more Fc receptors and/or to C1q by at least 2-fold, at least 5-fold, at least 10-fold, at least 20-fold or even at least 50-fold when compared to the wild-type Fc region. In alternative embodiments, the one or more amino acid substitutions may reduce the ability of the isolated antibody or antibody fragment according to the present disclosure to induce effector function by at least 2-fold, at least 5-fold, at least 10-fold, at least 20-fold or even at least 50-fold when compared to the wild-type Fc region.

In an embodiment, the variant Fc region of the humanized antibody or antibody fragment according to the present disclosure does not substantially bind to one or more Fc receptors and/or C1q. In an embodiment, the variant Fc region of the antibody according to the present disclosure does substantially abolish the ability of said antibody to induce effector function. In an embodiment, the antibody or antibody fragment according to the present disclosure does not substantially induce effector function. In an embodiment, said effect function is ADCC and/or ADCP and/or CDC. In an embodiment, the antibody or antibody fragment according to the present disclosure does not substantially induce effector function meaning that the level of induced effector function is not significantly above the background as measured in the absence of said antibody.

In an embodiment, the Fc receptor is a human Fc receptor. In an embodiment, the Fc receptor is an Fcy receptor. In an embodiment, the Fc receptor is a human FcyRIIIa, FcyRI, FcyRIIa and/or FcvRIIb.

In an embodiment, the humanized antibody or antibody fragment according to the present disclosure comprises a variant human IgG1 Fe region, which comprises one or more amino acid substitutions compared to the wild-type human IgG1 Fc region. In an embodiment, that one or more amino acid substitutions reduce or abolish the binding of the variant Fc region to an Fc receptor and/or to C1q and/or reduces the ability of said antibody to induce effector function when compared to the wild-type Fc region.

The humanized antibody or antibody fragment according to the present disclosure may or may not be fused to one or more other amino acid residues, polypeptides or moieties. Such a fusion protein may be prepared in any suitable manner, including genetically or chemically approaches. Said linked moieties may contain secretory or leader sequences, sequences that aid detection, expression, separation or purification, or sequences that confer to increased protein stability, for example, during recombinant production. Non-limiting examples of potential moieties include beta-galactosidase, glutathione-S-transferase, luciferase, a T7 polymerase fragment, a secretion signal peptide, an antibody or antibody fragment, a toxin, a reporter enzyme, a moiety being capable of binding a metal ion like a poly-histidine tag, a tag suitable for detection and/or purification, a homo- or hetero-association domain, a moiety which increases solubility of a protein, or a moiety which comprises an enzymatic cleavage site.

Accordingly, the humanized antibody or antibody fragment according to the present disclosure may optionally contain one or more moieties for binding to other targets or target proteins of interest. It should be clear that such further moieties may or may not provide further functionality to the antibody and may or may not modify the properties of the isolated antibody or antibody fragment according to the present disclosure.

Therapeutic Methods

The humanized antibody or antibody fragment according to the present disclosure may be used in therapeutic methods. The antibody or antibody fragment according to the present disclosure may be used for the treatment of inflammatory diseases, autoimmune diseases, fibrotic diseases, hematologic malignancies and potentially other diseases.

In an embodiment, the disease is associated with the undesired presence of human IL3. In another embodiment, the disease is associated with the undesired presence of IL3 expressing cells, in particular human IL3 expressing T cells.

IL3 has a significant growth stimulating and differentiating effect on various hematopoietic precursor cells and is also a growth factor for mast cells. The signal transduction caused by IL3 has major impact on the immune system. Any disease or medical condition in which IL3 plays a direct or indirect role in development or progression is a candidate for the treatment by administering the antibodies according to the present disclosure. Preferably such disease or malfunction connected with elevated levels of IL3 or elevated expression of IL3 by cells capable of producing IL3 such as T cells, basophils, B cells. NK cells, certain types of cancers/tumors, neurons, and others is related to the immune system, mostly an autoimmune, inflammatory or fibrotic disease and especially systemic lupus, systemic sclerosis, RA, PsA or acute or chronic graft-versus-host disease and multiple sclerosis, acute or chronic allograft rejection.

In an embodiment, the disease to be treated is an autoimmune or inflammatory disease. Non-limiting examples an autoimmune or inflammatory diseases include rheumatoid arthritis (RA), psoriasis, psoriatic arthritis, systemic lupus erythematosus (SLE), lupus nephritis, type I diabetes. Grave's disease, Inflammatory bowel disease (IBD), Crohn's disease (CD), ulcerative colitis (UC), irritable bowel syndrome, multiple sclerosis (MS), Guillain-Barré's Syndrome, autoinflammatory diseases like Familial Mediterranean Fever (FMF), Cryopyrin-associated periodic syndromes (CAPS). Deficiency of IL-1-Receptor Antagonist (DIRA), Hyper IgD Syndrome (HIDS), autoimmune myocarditis, Kawasaki disease, coronary artery disease, chronic obstructive pulmonary disease (COPD), interstitial lung disease, autoimmune thyroiditis, scleroderma, systemic sclerosis, osteoarthritis, atopic dermatitis, vitiligo, graft vs. host disease, Sjogren's syndrome, autoimmune nephritis, Goodpasture's syndrome, chronic inflammatory demyelinating polyneuropathy, ANCA-associated vasculitis, uveitis, scleroderma, bullous pemphigoid, Alzheimer's Disease, amyotrophic lateral sclerosis, Huntington's Chorea, cystic fibrosis, gout, age-related macular degeneration, allergy, asthma, antiphospholipid syndrome (APS), atherosclerosis, C3 glomerulopathy and IgA nephropathy, ischemia/reperfusion injury, peritonitis, sepsis and other autoimmune diseases that are a result of either acute or chronic inflammation.

In an embodiment, the disease to be treated is a proliferative disease. In a particular embodiment, the disease is cancer. Non-limiting examples of cancers include hematologic malignancies like chronic myelomonocytic leukemia (CMML), acute myeloid leukemia (AML), myelodysplastic syndrome, mastocytosis, basophil leukemia, pDC cancers and non-hematologic malignancies like bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, sarcoma, skin cancer, squamous cell carcinoma, bone cancer, melanoma, renal cell carcinoma, and kidney cancer.

Further circumstances which are preferably treated by administering the pharmaceutical composition according to the invention is a use in suppressing the activity of human basophils in persons suffering from an allergic reaction and for the stratification of patients having increased IL3 levels in serum or plasma or elevated expression of IL3 by cells capable of producing IL-3 (e.g. T cells).

Especially in view of RA it has been found that for a large group of patients elevated levels of hIL3 produced by T cells are correlated with the aggravation caused in the patient and the progression of the disease. IL3 is detected mainly in active RA, whereas patients with a non-active stage of RA usually do not show elevated expression or elevated levels of IL3. Thus the pharmaceutical compositions of the present invention are especially useful in treating patients with active episodes of autoimmune diseases, such as RA, and for the prophylactic treatment to avoid the occurrence of active episodes of the disease.

Since available therapies are only effective in about 50% of treated patients, providing the pharmaceutical compositions according to the invention is a major step to a new and gentle treatment of auto-immune disease in patients. Based on the lack of an overt phenotype of IL3 deficient mice (Nature (1998) 392:90-3) and no obvious side effects of mice treated with antibodies against IL3 (Arthritis Rheum (2009) 60:1352-61) IL-3 targeted treatment should exhibit less severe side effects than currently used pharmaceuticals, especially regarding to infection or neoplasia. In certain cases, it could be desirable to combine treatment with the antibodies and pharmaceutical compositions of the present invention with other medicines like methotrexate or leflunomide. An individualized treatment strategy according to IL3 expression or IL3 levels in plasma, serum or other body fluids, presents an advantage compared to available biologicals, since currently it is not possible to predict reliably, which patient will respond to a specific therapy (including biologicals). Further an individualized approach improves the safety of treatment by reducing the risk of side effects of an ineffective therapy and reduces the costs for treatment of RA.

Also the treatment with the antibodies of the present invention would preferentially be started as soon as elevated expression of IL3 or elevated IL3 levels in blood, plasma or serum are detected. Thus, early-on treatment can be applied in patients where RA activity is correlated with elevated hIL-3 levels and long term joint damage can be avoided or kept to a minimum. In addition, treatment with anti-IL3 antibodies would preferentially be started, if patients failed to a previous treatment with DMARDs or biologicals. Further it is expected that the use of the antibodies of the invention can reduce cell infiltration of synovial tissue which can be a further negative factor in the disease pathology.

In an embodiment, the present disclosure provides a method for the treatment of a disease.

In an embodiment, the present disclosure provides a method for the treatment of a disease comprising administering to a patient an antibody or antibody fragment of the present disclosure.

In an embodiment, the present disclosure provides a method for the treatment of a disease comprising administering to a subject in need there of an antibody or antibody fragment of the present disclosure.

In an embodiment, the present disclosure provides a method for the prevention of a disease.

In an embodiment, the present disclosure provides a method for the prevention of a disease comprising administering to a subject an antibody or antibody fragment of the present disclosure.

In an embodiment, the present disclosure provides a humanized antibody or antibody fragment according to the present disclosure for the treatment of a disease. In an embodiment, the present disclosure provides a humanized antibody or antibody fragment according to the present disclosure for use in the treatment of a disease. In an embodiment, the present disclosure provides a humanized antibody or antibody fragment according to the present disclosure for use in the treatment of a disease in a subject in need thereof.

In an embodiment, the present disclosure provides the use of an antibody or antibody fragment according to the present disclosure for the manufacture of a medicament. In an embodiment, the present disclosure provides a humanized antibody or antibody fragment according to the present disclosure for use as a medicament. In an embodiment, the present disclosure provides a humanized antibody or antibody fragment according to the present disclosure for use in medicine. In an embodiment, the present disclosure provides a humanized antibody or antibody fragment according to the present disclosure for use as a medicament for the treatment of a subject in need thereof.

In an embodiment, the present disclosure provides a humanized antibody or antibody fragment specific for human IL3 according to the present disclosure for use in a method of treating a subject having a disease comprising administering to the subject a therapeutically effective amount of an antibody or antibody fragment according to the present disclosure.

In an embodiment, the method further comprises administering to the subject a therapeutically effective amount of at least one additional therapeutic agent. The subject in need of treatment is typically a mammal, more specifically a human. For use in therapeutic methods, a humanized antibody or antibody fragment according to the present disclosure would be formulated, dosed, and administered in a way consistent with good medical practice.

Pharmaceutical Compositions

In an embodiment, the present disclosure provides a pharmaceutical composition comprising an isolated antibody or antibody fragment according to the present disclosure and a pharmaceutically acceptable carrier or excipient.

The pharmaceutical compositions may further comprise at least one other pharmaceutically active compound. The pharmaceutical composition according to the present disclosure can be used in the diagnosis, prevention and/or treatment of diseases associated with the undesired presence of IL3, in particular human IL3. The pharmaceutical composition according to the present disclosure can be used in the diagnosis, prevention and/or treatment of diseases associated with the undesired presence of IL3 positive cells, in particular IL3 positive human cells. In particular, the present disclosure provides a pharmaceutical compositions comprising an antibody or antibody fragment according to the present disclosure that is suitable for prophylactic, therapeutic and/or diagnostic use in a mammal, more particular in a human.

In general, an antibody or antibody fragment according to the present disclosure may be formulated as a pharmaceutical composition comprising at least one antibody or antibody fragment according to the present disclosure and at least one pharmaceutically acceptable carrier or excipient, and optionally one or more further pharmaceutically active compounds. Such a formulation may be suitable for oral, parenteral, topical administration or for administration by inhalation. Accordingly, a pharmaceutical composition comprising at least one antibody or antibody fragment according to the present disclosure may be administered parenterally, such as intravenously, or intramuscularly, or subcutaneously. Alternatively, an antibody of the invention may be administered via a non-parenteral route, such as per-orally or topically. In a preferred embodiment, a pharmaceutical composition comprising an antibody or antibody fragment according to the present disclosure is administered intravenously or subcutaneously.

In particular, an antibody or antibody fragment according to the present disclosure may be used in combination with one or more pharmaceutically active compounds that are or can be used for the prevention and/or treatment of the diseases in which a target antigen of interest is involved, as a result of which a synergistic effect may or may not be obtained. Examples of such compounds, as well as routes, methods and pharmaceutical formulations or compositions for administering them will be clear to the clinician.

In an embodiment, the present disclosure provides a pharmaceutical composition comprising an antibody or antibody fragment according to the present disclosure for use in the prevention and/or treatment of a disease associated with the undesired presence of IL3, in particular human IL3. In an embodiment, the present disclosure provides a pharmaceutical composition comprising an antibody or antibody fragment according to the present disclosure for use in the prevention and/or treatment of a disease associated with the undesired presence of IL3positive cells, in particular IL3positive human cells. In an embodiment, the present disclosure provides a pharmaceutical composition comprising an antibody or antibody fragment according to the present disclosure for the use as a medicament. In an embodiment, the present disclosure provides a pharmaceutical composition comprising an antibody or antibody fragment according to the present disclosure for use in the prevention and/or treatment of an autoimmune disease and/or inflammatory disease and/or cancer.

In an embodiment, the present disclosure provides a method for the treatment of an autoimmune disease and/or inflammatory disease and/or cancer in a subject in need thereof using a pharmaceutical composition comprising an antibody or antibody fragment according to the present disclosure.

Further provided is a method of producing an antibody or antibody fragment according to the present disclosure in a form suitable for administration in vivo, the method comprising (a) obtaining an antibody or antibody fragment by a method according to the present disclosure, and (b) formulating said antibody or antibody fragment with at least one pharmaceutically acceptable carrier or excipient, whereby a preparation of antibody or antibody fragment is formulated for administration in vivo. Pharmaceutical compositions according to the present disclosure comprise a therapeutically effective amount of one or more antibodies or antibody fragments according to the present disclosure dissolved in a pharmaceutically acceptable carrier or excipient.

Diagnostic Use

In an embodiment, the present disclosure provides the use of a humanized antibody or antibody fragment specific for human IL3 according to the present disclosure for the diagnosis of a disease. In an embodiment, the present disclosure provides the use of an antibody or antibody fragment according to the present disclosure for the detection of IL3, in particular human IL3. In an embodiment, the present disclosure provides a method for detecting IL3 in a subject or a sample, comprising the step of contacting said subject or sample with a humanized antibody or antibody fragment specific for human IL3 of the present disclosure. In an embodiment, the present disclosure provides a method for diagnosing a disease in a subject, comprising the step of contacting said subject or sample with a humanized antibody or antibody fragment according to the present disclosure. The antibodies may also be used to determine IL3 expression levels in cells from patients. The IL3 expressions levels may serve as therapeutic biomarkers, for example for patient stratification.

EXAMPLES

Example 1: Parental antibody P8C11 (DSM ACC3281)

The parental mouse antibody P8C11 was originally produced by immunizing Balb/c mice with human eukaryotic glycosylated IL-3: see WO2017/081218. The antibody was deposited at the DSMZ on Oct. 7, 2015 (DSM ACC3281).

P8C11 is a mouse IgG1 monoclonal antibody. The sequence of the variable heavy chain (IGHV1S137*01) the variable light chain (IGKV15-103*01) and the CDRs is shown m Table 1 below. The variable heavy chain of antibody P8C11 has three mutations compared to the germline sequence: M instead of L, A instead of S and I instead of V. These positions are indicated in SEQ ID No. 2 below

TABLE 1

| | | |
|---|---|---|
| VH | QVQLQQSGAEMVRPGVSVKIACKGSGFTFTDYAL HWVKQSHAKSLEWIGLISTYYGDTTYNQRFKGKA TMTVDKSSSTAYMELARLTSEDSAIYYCVITTVA GTDAMDYWGQGTSVTVSS | SEQ ID No. 2 |
| HCDR1 (Kabat) | DYALH | SEQ ID No. 3 |
| HCDR2 (Kabat) | LISTYYGDTTYNQRFKG | SEQ ID No. 4 |
| HCDR3 (Kabat) | TTVAGTDAMDY | SEQ ID No. 5 |
| HCDR1 (IMGT) | GFTFTDYA | SEQ ID No. 6 |
| HCDR2 (IMGT) | ISTYYGDT | SEQ ID No. 7 |
| HCDR3 (IMGT) | VITTVAGTDAMDY | SEQ ID No. 8 |
| VL | DIQMNQSPSSLSASLGDTITITCHASQNINVWLS WYQQKPGNIPKLLIYKASNLHTGVPSRFSGSGSG TGFTLTISSLQPEDIATYYCQQGYSYPYTFGGGT KLEIK | SEQ ID No. 9 |
| LCDR1 (Kabat) | HASQNINVWLS | SEQ ID No. 10 |
| LCDR2 (Kabat) | KASNLHT | SEQ ID No. 11 |
| LCDR3 (Kabat) | QQGYSYPYT | SEQ ID No. 12 |
| LCDR1 (IMGT) | QNINVW | SEQ ID No. 13 |
| LCDR2 (IMGT) | KAS | |
| LCDR3 (IMGT) | QQGYSYPYT | SEQ ID No. 12 |

Antibody P8C11 was originally produced by immunizing Balb/c mice with human eukaryotic glycosylated IL-3, see WO2017/081218. The antibody was deposited at the DSMZ on Oct. 7, 2015 (DSM ACC3281). P8C11 inhibits the IL3 dependent growth of TF1 cells and numerous other beneficial activities which indicate that P8C11 could be candidate for clinical development (WO2017/081218).

Example 2: Humanization of Antibody P8C11

Example 2.1: Grafting of the CDRs onto New Framework Sequences

In a first step, the CDRs of P8C11 were grafted into the frameworks of the three most closely related human germline genes—IGKV1-12*01, IGKV1-33*01 and IGKV1-27*01 for the variable light chain. For the variable heavy chain, IGHV1-3*01 and IGHV7-4-1*02 were selected, as well as a IGHV1-3*01 variant, in which the germline mutations of SEQ ID No. 2 were included and one alanine residues was back-mutated to the originally glycine residue, because this amino acid was close to the HCDR1 Sequences of the variable light chains and the variable heavy chains are shown in the following table.

TABLE 2

LC1 Human germ line IGKV1-12*01
DIQMTQSPSSVSASVGDRVTITCHASQNINVWLSWYQQKPGKAPKLLIYK
ASNLHTGVPSRFSGSGSGTDFTLTISSLQPEDFATYYCQQGYSYPYTFGG
GTKLEIK (SEQ ID No. 15)

LC2 Human germ line IGKV1-33*01
DIQMTQSPSSLSASVGDRVTITCHASQNINVWLSWYQQKPGKAPKLLIYK
ASNLHTGVPSRFSGSGSGTDFTFTISSLQPEDIATYYCQQGYSYPYTFGG
GTKLEIK (SEQ ID No. 16)

LC3 Human germ line IGKV1-27*01
DIQMTQSPSSLSASVGDRVTITCHASQNINVWLSWYQQKPGKVPKLLIYK
ASNLHTGVPSRFSGSGSGTDFTLTISSLQPEDVATYYCQQGYSYPYTFGG
GTKLEIK (SEQ ID No. 17)

HC1 Human germ line IGHV1-3*01
QVQLVQSGAEVKKPGASVKVSCKASGFTFTDYALHWVRQAPGQRLEWMGL
ISTYYGDTTYNQRFKGRVTITRDTSASTAYMELSSLRSEDTAVYYCVITT
VAGTDAMDYWGQGTLVTVSS (SEQ ID No. 18)

HC2 Human germ line IGHV7-4-1*02
QVQLVQSGSELKKPGASVKVSCKASGFTFTDYALHWVRQAPGQGLEWMGL
ISTYYGDTTYNQRFKGRFVFSLDTSVSTAYLQISSLKAEDTAVYYCVITT
VAGTDAMDYWGQGTLVTVSS (SEQ ID No. 19)

HC3 Human germ line IGHV1-3*01 with mouse germ
line reversions back-mutation
QVQLVQSGAEMKKPGASVKVACKGSGFTFTDYALHWVRQAPGQRLEWMGL
ISTYYGDTTYNQRFKGRVTITRDTSASTAYMELSSLRSEDTAIYYCVITT
VAGTDAMDYWGQGTLVTVSS (SEQ ID No. 20)

All three variable heavy chain were paired with all three variable light chains, yielding in nine different antibodies. The inhibitory activity of these nine, antibodies, was tested and compared to that of a chimeric version of P8C11 (an antibody carry the variable murine heavy and light chain of P8C11 fused to human IgG1 kappa). Inhibitory activity was measured by analyzing the ability of the antibody variants to block IL-3 induced downregulation of CD131 on primary human basophils. IL-3 (0.2 ng/ml) was preincubated for 1 h at 37° C., with various concentrations of chimeric P8C11 or humanized variants or PBS as control and then added to whole human EDTA blood for 1 h at 37° C. In a separate vial only PBS (no IL-3) was added to whole human EDTA blood for 1 h at 37° C., to induce no downregulation of CD131. Then the blood was stained with directly antibodies against CD123, CD203c and CD131 for 30 min on ice to identify basophils and to measure the surface level of CD131 on basophils. The inhibitory activity of chimeric P8C11 was normalized to 100%, the inhibitory activity of PBS in the absence of any antibody was normalized to 0%. If the concentration of a humanized variant needed to be 10-fold higher than the concentration of chimeric P8C11 to reach the same level of inhibition of CD31 downregulation, the inhibitory, activity was determined to be 10%.

Inhibitory activities are shown in the following Table.

TABLE 3

| Construct | Inhibitory activity |
|---|---|
| Chimeric P8C11 | 100% |
| HC1 × LC1 | 2% |
| HC1 × LC2 | 2% |
| HC1 × LC3 | 2% |
| HC2 × LC1 | 0.5% |
| HC2 × LC2 | 0.5% |
| HC2 × LC3 | 0.5% |
| HC3 × LC1 | 6% |
| HC3 × LC2 | 6% |
| HC3 × LC3 | 6% |

None of the nine humanized antibodies had an inhibitory activity that came close to that of chimeric P8C11. Among the three variable heavy chains. HC3 was the best variant to proceed. The three variable light chains were equally effective. LC2 was chosen for further humanization.

Example 2.2: Identification of the Variable Chain Responsible for Loss of Activity Next, in order to investigate if the variable heavy chain or the variable light chain acceptor framework is responsible for the loss of inhibitory activity, the murine variable heavy chain was paired with the variable light chain VL2 (muHC×LC2), and the murine variable light chain was paired with the variable heavy chain HC3 (HC3×muLC). Inhibitory activity was again compared to chimeric P8C11. Results are shown in the following table.

TABLE 4

| Construct | Inhibitory activity |
|---|---|
| Chimeric P8C11 | 100% |
| MuHC × LC2 | 100% |
| HC3 × MuLC | 6% |

This result indicated that the loss of inhibitory activity is due to the humanization of the variable heavy chain, but not a result of the humanization of the variable light chain.

Example 2.3: Identification of the Critical Framework within HC3

In order to investigate which part of the framework is responsible for the loss of inhibitory activity, various hybrid framework were constructed, consisting either of the original mouse framework or the respective parts of the humanized framework of HC3.

Generated were the three, constructs shown in the following table.

TABLE 5

```
HC3.MMH
FRI: murine  FR2: murine FR3: HC3    FR4: HC3
QVQLQQSGAEMVRPGVSVKIACKGSGFTFTDYALHWVKQSHAKSLEWIGL
ISTYYGDTTYNQRFKGRVTITRDTSASTAYMELSSLRSEDTAIYYCVITT
VAGTDAMDYWGQGTLVTVSS (SEQ ID No. 21)

HC3.MHM
FRI: murine  FR2: HC3    FR3: marine FR4: murine
QVQLQQSGAEMVRPGVSVKIACKGSGFTFTDYALHWVRQAPGQRLEWMGL
ISTYYGDTTYNQRFKGKATMTVDKSSSTAYMELARLTSEDSAIYYCVITT
VAGTDAMDYWGQGTSVTVSS (SEQ ID No. 22)

HC3.HMM
FRI: HC3    FR2: murine FR3: murine FR4: murine
QVQLVQSGAEMKKPGASVKVACKGSGFTFTDYALHWVKQSHAKSLEWIGL
ISTYYGDTTYNQRFKGKATMTVDKSSSTAYMELARLTSEDSAIYYCVITT
VAGTDAMDYWGQGTSVTVSS (SEQ ID No. 23)
```

These variable heavy chains were paired with the murine variable light chain of P8C11 and the inhibitory activity was measured. Results are shown in the following table.

TABLE 6

| Construct | Inhibitory activity |
|---|---|
| Chimeric P8C11 | 100% |
| HC3.MMH × muLC | 4% |

TABLE 6-continued

| Construct | Inhibitory activity |
|---|---|
| HC3.MHM × muLC | 100% |
| HC3.HMM × muLC | 100% |

This result indicates that framework 3 (FR3) of HC3 is responsible for the loss of inhibitory activity Framework 4 (FR4) of HC3 is very unlikely to be responsible, as only one amino acid differs from the original mouse framework sequence, and FR4 usually does not contribute much to VH function.

Example 2.4: Identification of the Critical Residues within Framework 3 of HC3

In order to investigate which part of framework 3 in HC3 is responsible for the loss of inhibitory activity, various hybrids of framework 3 were generated. All constructs had identical framework regions 1 and 2 and also all three CDRs were identical. In one construct, HC4, the first ten amino acids of framework 3 were that of the original mouse framework, the remaining amino acids were that of the human germline sequence IGHV1-3*01 (except for one isoleucine residue which corresponds to a germline mutation of the originator mouse antibody P8C11) In one construct. HC5, the first ten amino acids of framework 3 were that of the human germline sequence IGHV1-3*01 and the remaining amino acids were that of the original mouse framework. In a third construct, HC6, framework 3 is composed of a hybrid IGHV1-18*01 and IGHV1-69*02, which both share similarity with the original mouse framework of P8C11 at the N-terminus and the C-terminus, respectively. Again, the isoleucine residue in framework 3, which corresponds to a germline mutation of the originator mouse antibody P8C11, was kept. In addition, the "murine" valine at position 6 of framework 3 and the "murine" serine at position 10 of framework 3 were kept.

The amino acid sequences of three constructs are shown in the following table.

TABLE 7

```
HC4
QVQLVQSGAEMKKPGASVKVACKGSGFTFTDYALHWVRQAPGQRLEWMGL
ISTYYGDTTYNQRFKGKATMTVDKSSSTAYMELSSLRSEDTAIYYCVITT
VAGTDAMDYWGQGTLVTVSS (SEQ ID No. 24)

HC5
QVQLVQSGAEMKKPGASVKVACKGSGFTFTDYALHWVRQAPGQRLEWMGL
ISTYYGDTTYNQRFKGRVTITRDTSASTAYMELARLTSEDSAIYYCVITT
VAGTDAMDYWGQGTSVTVSS (SEQ ID No. 25)

HC6
QVQLVQSGAEMKKPGASVKVACKGSGFTFTDYALHWVRQAPGQRLEWMGL
ISTYYGDTTYNQRFKGRVTMTVDKSSSTAYMELSSLRSEDTAIYYCVITT
VAGTDAMDYWGQGTLVTVSS (SEQ ID No. 26)
```

These variable heavy, chains were paired with the humanized variable light chain VL2 and the inhibitory activity was measured. Results are shown in the following table.

TABLE 8

| Construct | Inhibitory activity |
|---|---|
| Chimeric P8C11 | 100% |
| HC4 × LC2 | 100% |

TABLE 8-continued

| Construct | Inhibitory activity |
| --- | --- |
| HC5 × LC2 | 9% |
| HC6 × LC2 | 100% |

Comparison of the heavy chains HC4 and HC5 show that the first 10 amino acids of framework region 3 are critical to preserve activity of the antibody. If these 10 amino acids have the original mouse sequence the antibody is fully active. Also H6, which has a similar amino acid sequence at this location, fully preserves activity.

Example 2.5: Optimization of HC6 to Increase Humanness

Four different heavy chains were designed based on HC6 in order to further increase the humanness. HC7 and HC8 are both based on HC6 but have less residual mouse framework-sequences. HC9 and HC10 are also both based on HC6 but are closer to germline IGHV1-3*01.

The amino acid sequences of four constructs are shown in the following table.

TABLE 9

HC7
QVQLVQSGAEVKKPGASVKVACKGSGFTFTDYALHWVRQAPGQRLEWMGL
ISTYYGDTTYNQRFKGRVTMTVDKSSSTAYMELSSLRSEDTAVYYCVITT
VAGTDAMDYWGQGTLVTVSS (SEQ ID No. 27)

HC8
QVQLVQSGAEMKKPGASVKVSCKASGFTFTDYALHWVRQAPGQRLEWMGL
ISTYYGDTTYNQRFKGRVTMTVDKSSSTAYMELSSLRSEDTAIYYCVITT
VAGTDAMDYWGQGTLVTVSS (SEQ ID No. 28)

HC9
QVQLVQSGAEMKKPGASVKVACKGSGFTFTDYALHWVRQAPGQRLEWMGL
ISTYYGDTTYNQRFKGRVTMTVDKSASTAYMELSSLRSEDTAIYYCVITT
VAGTDAMDYWGQGTLVTVSS (SEQ ID No. 29)

HC10
QVQLVQSGAEMKKPGASVKVACKGSGFTFTDYALHWVRQAPGQRLEWMGL
ISTYYGDTTYNQRFKGRVTITVDKSASTAYMELSSLRSEDTAIYYCVITT
VAGTDAMDYWGQGTLVTVSS (SEQ ID No. 30)

Again, these variable heavy chains were paired with the humanized variable light chain VL2 and the inhibitory activity was measured. Results are shown in the following table.

TABLE 10

| Construct | Inhibitory activity |
| --- | --- |
| Chimeric P8C11 | 100% |
| HC7 × LC2 | 100% |
| HC8 × LC2 | 25% |
| HC9 × LC2 | 50% |
| HC10 × LC2 | 40% |

Comparison of the heavy chains HC7 and HC8 shows that the residual mouse-derived amino acids A and G in framework 1 are important for activity, while the residual mouse-derived amino acids M in framework 1 and I in framework 3 are not essential for activity. Comparison of the heavy chains HC9 and HC10 shows that at position 4 in framework 3, the amino acid M results in a slightly higher activity than amino acid 1.

Example 2.6: Optimization of HC7 to Increase Humanness

Six additional different heavy chains were designed based on HC7 in order to further increase the humanness.

The amino acid sequences of three constructs are shown in the following table.

TABLE 11

H11
QVQLVQSGAEVKKPGASVKVACKGSGFTFTDYALHWVRQAPGQRLEWMG
LISTYYGDTTYNQRFKGRVTMTADKSTSTAYMELSSLRSEDTAVYYCVI
TTVAGTDAMDYWGQGTLVTVSS (SEQ ID No. 31)

H12
QVQLVQSGAEVKKPGASVKVACKGSGFTFTDYALHWVRQAPGQRLEWMG
LISTYYGDTTYNQRFKGRVTMTVDKSTSTAYMELSSLRSEDTAVYYCVI
TTVAGTDAMDYWGQGTLVTVSS (SEQ ID No. 32)

HC13
QVQLVQSGAEVKKPGASVKVACKGSGFTFTDYALHWVRQAPGQRLEWMG
LISTYYGDTTYNQRFKGRVTMTADKSSSTAYMELSSLRSEDTAVYYCVI
TTVAGTDAMDYWGQGTLVTVSS (SEQ ID No. 33)

HC14
QVQLVQSGAEVKKPGASVKVSCKGSGFTFTDYALHWVRQAPGQRLEWMG
LISTYYGDTTYNQRFKGRVTMTADKSTSTAYMELSSLRSEDTAVYYCVI
TTVAGTDAMDYWGQGTLVTVSS (SEQ ID No. 34)

HC15
QVQLVQSGAEVKKPGASVKVACKASGFTFTDYALHWVRQAPGQRLEWMG
LISTYYGDTTYNQRFKGRVTMTADKSTSTAYMELSSLRSEDTAVYYCVI
TTVAGTDAMDYWGQGTLVTVSS (SEQ ID No. 35)

HC16
QVQLVQSGAEVKKPGASVKVSCKGSGFTFTDYALHWVRQAPGQRLEWMG
LISTYYGDTTYNQRFKGRVTMVDKSTSTAYMELSSLRSEDTAVYYCVI
TTVAGTDAMDYWGQGTLVTVSS (SEQ ID No. 36)

Again, these variable heavy chains were paired with the humanized variable light chain VL2 and the inhibitory activity was measured. Results are shown in the following table

TABLE 12

| Construct | Inhibitory activity |
| --- | --- |
| Chimeric P8C11 | 100% |
| HC11 × LC2 | 25% |
| HC12 × LC2 | 100% |
| HC13 × LC2 | 25% |
| HC14 × LC2 | 25% |
| HC15 × LC2 | 8% |
| HC16 × LC2 | 100% |

Comparison of the heavy chains HC11 and HC12 shows that V at position 6 of framework 3 is important to preserve activity. A at position 6 of FR3 results in considerable loss of inhibitory activity.

Comparison of the heavy chains HC11 and HC13 shows that at position 10 of framework 3 the amino acids T and S result in similar inhibitory activity. T at position 10 of framework 3 is preferred to increase humanness.

Comparison of the heavy chains HC11, HC14 and HC15 shows that G at position 24 of framework 1 is important to preserve inhibitory activity and should not be replaced by A.

Comparison of the heavy chains HC11, HC14 and HC15 also shows that at position 21 of framework 1 the amino acid A is not important to preserve activity and can be replaced by S to increase humanness.

The heavy chain HC16 contains G at position 24 of framework 1. V at position 6 of framework 3 and T at position 10 of FR3. It shows full inhibitory activity and the best possible humanness.

Therefore, as final candidate an antibody was selected with comprises the heavy chain HC16 and the variable light chain LC2. This antibody received the designation "GRT002-H16L2" The antibody has the following heavy chain sequence:

(SEQ ID No. 44)
QVQLVQSGAEVKKPGASVKVSCKGSGFTFTDYALHWVRQAPGQRLEWMG

LISTYYGDTTYNQRFKGRVTMTVDKSTSTAYMELSSLRSEDTAVYYCVI

TTVAGTDAMDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPG and the following light chain sequence:

(SEQ ID No. 45)
DIQMTQSPSSLSASVGDRVTITCHASQNINVWLSWYQQKPGKAPKLLIY

KASNLHTGVPSRFSGSGSGTDFTFTISSLQPEDIATYYCQQGYSYPYTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

Example 2.7: Summary of the Humanization Process

Humanization of P8C11 was far from straight forward. In the end, a six-step iterative process had to be set up to identify a humanized derivative of P8C11 which retained the desire activity. i.e. inhibition of glycosylated IL3. During this process three different variable light chains and sixteen different variable heavy chains were generated that were tested in various combinations. Various critical amino acids were identified that are required for full binding and inhibition of IL-3. Many of these residues are directly adjacent to the CDR regions.

GRT002-H16L2 was identified as the final humanized variant of P8C11. The framework of the variable light chain of GRT002-H16L2 is 100% identical to human germline. Two amino acids in the framework of the variable heavy chain of GRT002-H16L2 are not identical to human germline. These two amino acids are essential for full binding and inhibition of IL-3. GRT002-H16L2 is an IgG1 antibody of the G1m3 (heavy chain) and KM3 (light chain) allotype which lacks the C-terminal lysine.

Example 3: Generation and Purification of GRT002-H16L2

Antibody GRT002-H16L2 was expressed and purified by Evitria A G (Schlieren, Switzerland) using standard technologies. Briefly, CHO cells were stably transfect with vectors encoding the GRT002-H16L2 antibody. Cells were grown in serum-free medium. Expression levels were >100 mg/l. The antibody was purified with Protein A (Schlieren. Switzerland). The antibody was dissolved at a concentration of 7.75 mg/ml in PBS plus 100 mM L-arginine and stored in aliquots at −20° C., until further use.

The antibody preparation had a monomer content of >97%. The molecular weight was 152.12 kDa as determined by SEC, utilizing 8 marker proteins.

Example 4: Determination of the Binding Properties of GRT002-H16L2

The binding properties of antibody GRT002-H16L2 were determined in comparison to the parental antibody P8C11 by surface plasmon resonance (SPR) using a Biacore X100 instrument (GE Healthcare) Chimeric antibody P8C11 was used as a reference. Antibodies were covalently bound to a CM5 sensor chip via a dextran matrix. Degassed PBS+ 0.05% Tween-20 was used as running buffer. Antibodies were used at a concentration of 1.5 µg/ml, the IL3 concentration was varied. Capturing was performed at a flow rate of 5 µl/min for 45 sec (sample cell only). After stabilization for 300 sec. IL3 was added at a flow rate of 15 µl/min for 360 sec (sample cell and reference cell). Dissociation time was 600 sec. Chips were regenerated with 10 mM Gly-HCl pH 1.5 for 30 sec and a flow rate of 30 µl/min, followed by a washing step with running buffer and 100 mM PBS pH 7.4 Data were analysed with the Biacore evaluation software, version 2.0.1. For affinity fitting the "Steady-state-affinity" model was used, for kinetic fitting the "1:1-binding" model.

Results are shown in FIG. 1. Based on the curves shown in FIG. 1, the binding properties could be determined and showed that the binding of antibody GRT002-H16L2 to IL-3 is the same or even slightly better than that of the parental antibody P8C11.

Example 5: Epitope Mapping of GRT002-H16L2

The epitope of GRT002-H16L2 was mapped by measuring the binding of the antibody to linear peptides derived from the amino acid sequence of IL3.

Peptides were coated overnight in PBS in Nunclon 96 Flat Bottom Transparent Polystyrol plates (Thermo Fisher) at a concentration of 10 µg/ml (60 µl/well). Then cells were washed three times with wash buffer (0.05% Tween 20 in PBS), followed by blocking for 2 hours at room temperature with 1% BSA/PBS. After another washing step with wash buffer, antibody GRT002-H16L2 was added (60 µl of a 10 µg/ml solution in 1% BSA/PBS) and incubated for 1 hour at room temperature. 1% BSA/PBS served as a control. After another washing step. GRT002-H16L2 was incubated with a secondary antibody (HRP-conjugated AffinePure fragment goat anti-human IgG: Jackson Immuno Research) for 1 hour at room temperature. After a final washing step, 100 µl of ABTS (2,2'-azino-bis(3-ethylbenzothiazoline-6-sulfonic acid) was added to each well. Absorption was measured in a infinite 200Pro reader (Tecan) at 405 nm.

For the parental antibody, P8C11, amino acids 22-48 of human IL3 (counted without signal sequence) were reported as the epitope (see WO2017/081218). The same epitope was confirmed for GRT002-H16L2. To further refine the epitope the following amino acids were tested.

TABLE 13

| Amino acids | | |
|---|---|---|
| mature | native | Sequence |
| 22-48 | 41-67 | EIITHLKQPPLPLLDFNNLNGEDQDIL (SEQ ID No. 37) |
| 26-48 | 45-67 | HLKQPPLPLLDFNNLNGEDQDIL (SEQ ID No. 38) |
| 28-48 | 47-67 | KQPPLPLLDFNNLNGEDQDIL (SEQ ID No. 39) |
| 30-48 | 49-67 | PPLPLLDFNNLNGEDQDIL (SEQ ID No. 40) |
| 22-42 | 41-61 | EIITHLKQPPLPLLDFNNING (SEQ ID No. 41) |
| 22-44 | 41-63 | EIITHLKQPPLPLLDFNNLNGED (SEQ ID No. 42) |
| 22-46 | 41-65 | EIITHLKQPPLPLLDFNNLNGEDQD (SEQ ID No. 43) |

Figure 2:
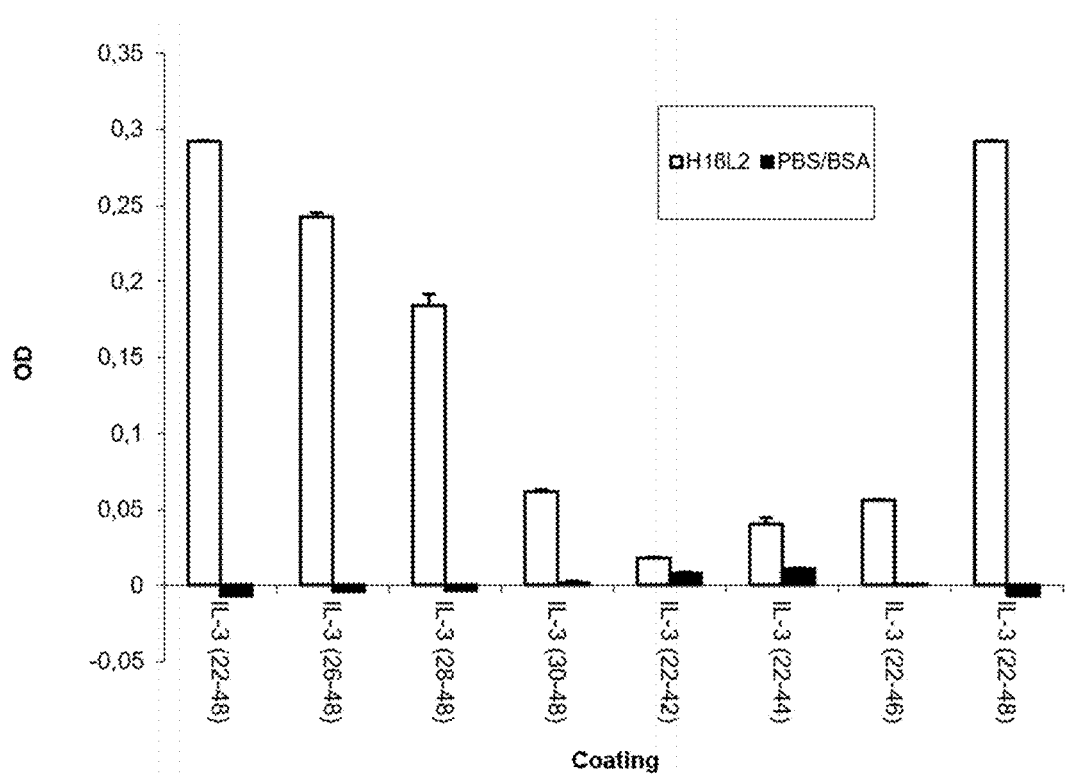
FIG. 2 shows the results of the epitope mapping for antibody GRT002-H16L2.

Results are shown in FIG. 2. The epitope of GRT002-H16L2 is identical to that of P8C11. Deletion of amino acids 47 and 48 of the tested peptide leads to a dramatic decrease of binding of GRT002-H16L2. GRT002-H16L2 still binds to peptides in which amino acids 22-25 or 22-27 are deleted, although too some slighter degree. In summary, GRT002-H16L2 binds to a linear epitope comprised in the amino acid sequence EIITHLKQPPLPLLDFNNLNGEDQDIL (SEQ ID No. 37).

Example 6: IL-3 Blockade in TF1 Cells

In a first experiment to analyze the ability of GRT002-H16L2 to block IL-3 activity. TF1 cells were used TF1 cells (ATCC, order no. #crl-2003) are human erythroblasts and the cell line has been established from bone marrow of a 35 year old male Japanese suffering from severe pancytopenia. Growth of TF1 cells is completely dependent on the presence of IL-3 or GMCSF. Thus, a test based on the cell proliferation of TF1 cells can be used to determine blocking of the IL-3 activity which in turn leads to a decrease or even a complete inhibition of the growth of TF1 cells.

Experimentally, a MTT-cell-proliferation assay is performed to determine the viability of cells based on the activity of the mitochondrial dehydrogenase. The dehydrogenase's substrate MIT (3-(4,5-dimethylthiazol-2-yl)-2,5-diphenyl tetrazolium bromide) which shows a yellow color in solution, is cleaved at the tetrazolium ring by the enzymatic activity leading to formation of purple MTT formazane crystals. Such crystals can be dissolved in isopropanol, the purple solution measured in a spectrometer and the results correlate to the amount of viable TF1 cells.

Cultivation of TF1 Cells:

TF1 cells were grown in suspension in a culture medium (RPMI-1640 containing 10% FCS (HIA), P/S and glutamine (1:100)) and supplemented with either 5 ng/ml of IL-3 or 5 ng/ml of GM-CSF) and split 1:4 every third day. For storage, cells were transferred from a cell culture bottle to 50 ml or 15 ml cell culture flasks (BD Falcon™). After centrifugation at 1400 rpm for 5 minutes at room temperature, the supernatant is completely removed. Cells are resuspended in culture medium (RPMI-1640 containing 10% FCS (HIA)+P/S+glutamine+5 ng/ml IL-3) and 5% DMSO and 1.5 ml aliquots are filled into vials. The cells are pre-frozen in a freezing container in a freezer at −80° C., and after 1-2 days transferred to a liquid nitrogen storage tank.

Blocking Experiment:

TF-1 cells that had been split every third day according to the protocol described above are split 1:2 in culture medium containing 5 ng/ml human IL-3 on the day before the experiment is performed. For the experiment, cells are centrifuged for 5 minutes at 1600 rpm at room temperature. The culture medium is removed and the cells washed twice in RPMI medium before cells are resuspended in 1 ml RPMI-1640+10% FCS (HIA)+P/S+glutamine (1:100), counted and supplemented with buffer to a final concentration of $1 \times 10^3$ cells/ml. In a 96-well-plate, 10,000 cells in 100 μl medium (RPMI+10% FCS+P/S+glutamine) are provided to each well. 100 μl of IL-3 which has been preincubated with the antibodies to be tested for 60 min at 37° C. For the preincubation different final concentrations of antibody and IL-3 are used. To obtain such final concentrations, the concentration of the antibody and IL-3 solutions needs to be twice the amount of the end concentration. After 5 days of incubation at 37° C., and addition of 5% CO2, 100 μl of medium are removed from each well and 10 μl MTT solution (LCG Standard-ATCC) are added to each well and the plates incubated for another 4 hours in an incubator at 37° C., and 5% CO2. After this further incubation, 100 μl MTT solvent is added and the contents of the wells mixed carefully. After an overnight incubation, optical density is determined at 570 and 690 nm and the number of viable cells calculated therefrom.

Figure 3:
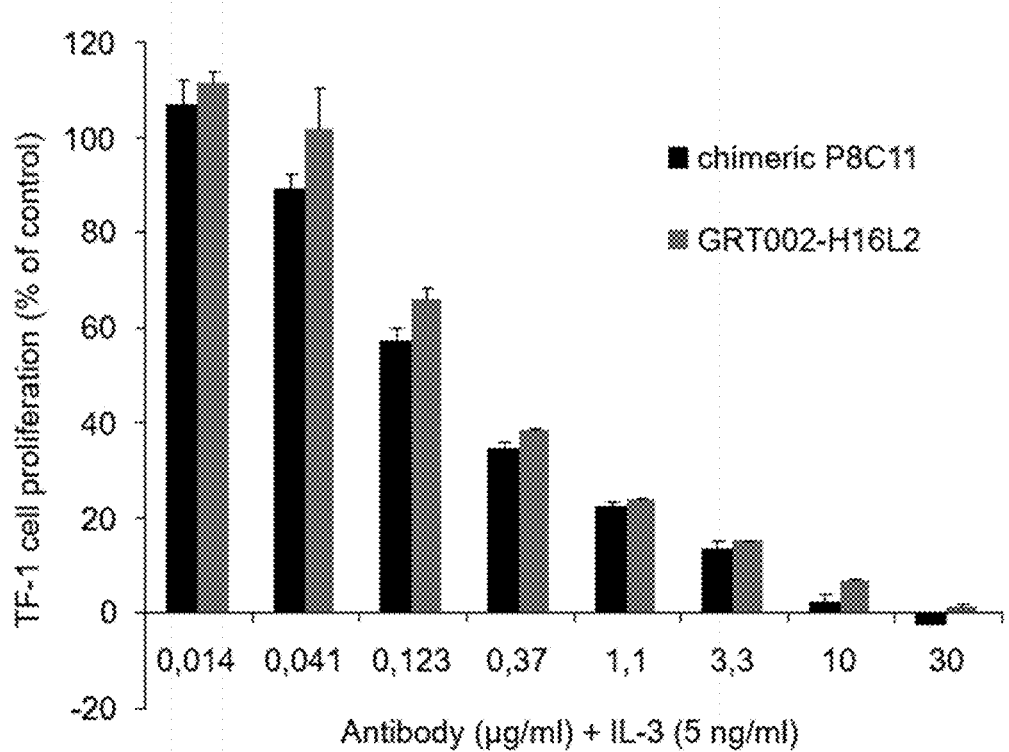
FIG. 3 shows that antibodies P8C11 and GRT002-H16L2 block IL-3 activity in TF1 cells to the same extent.

Experiments were performed for the chimeric antibody P8C11 and for antibody GRT002-H16L2 Results are shown in FIG. 3. Both antibodies block IL-3 activity in TF1 cells to the same extent.

Example 7: Blockade of IL-3 Binding to Human Basophils

To quantify blockade of binding of IL-3 to CD123 on basophil granulocytes via GRT002-H16L2 and PSC11-Chim a "IL-3 Biotinylated Fluorokine Flow Cytometry Kit" (R&D Systems) was used. Antibodies were used in various dilutions in 1% BSA/PBS. To 10 μl of the antibody solution 10 μl of biotinylated IL-3 (1 μg/ml) was added. Sample were preincubated for 30 min on ice in the dark. Thereafter 60 μl of EDTA-blood was added, followed by incubation for 60 min on ice in the dark. Then 20 μl Avidin-FITC, 3.33 μl CD123 PE-Cy 5.5 (1:30), and 1 μl CD203c PE (1:100) were added, followed by another incubation for 30 min on ice in the dark. After two washing steps, erythrocytes were lysed by adding 1 ml FACS-lysing solution for 10 min in the dark at room temperature. Thereafter samples were washed with PBS and centrifuged at 1,600 rpm and 4° C., for 6 min Samples were then analysed in a BD FACS Canto II instrument (Becton Dickinson) for 60 sec.

Figure 4:
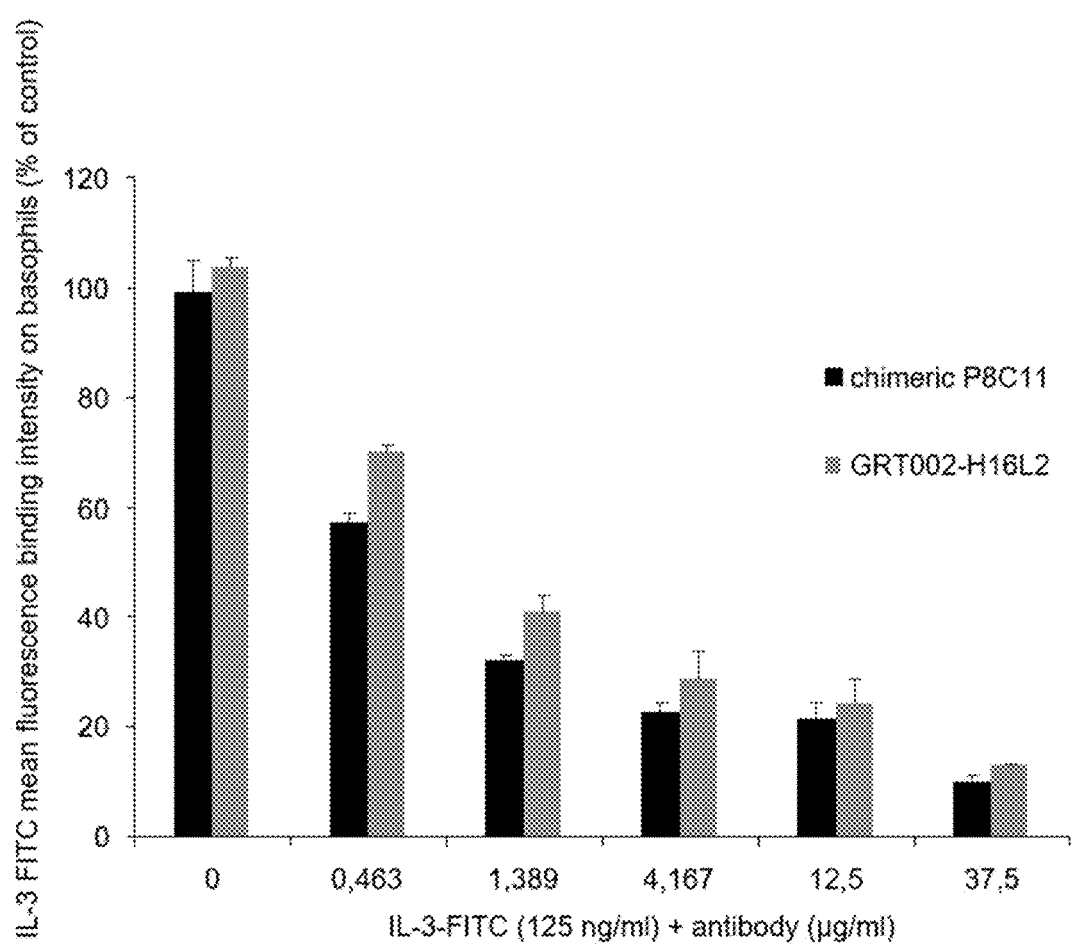
FIG. 4 shows that antibodies P8C11 and GRT002-H16L2 block IL-3 activity in human basophils to the same extent.

Results for antibodies P8C11 and GRT002-H16L2 are shown in FIG. 4. Both antibodies block IL-3 binding to human basophils to the same extent.

Example 8: Biophysical Properties of GRT002-H16L2

For clinical development it is crucial that an antibody has biophysical properties which make it possible to manufacture, store, formulate and administer the antibody in sufficient quantities without having any undesired effects like off-target stickiness. Antibody GRT002-H16L2 was therefore tested in a series of assays and compared to parental antibody P8C11.

Example 8.1: Melting Temperature

Melting points were determined by DSC (differential scanning calometry) using a Microcal VP-DSC mnstrument (Malvern). All samples were degassed (Microcal Thermovac, Malvern). Samples were measured in a temperature range from 25-130° C.: temperature was increased at 1° C., per minute. Antibodies were in a solution of PBS plus 100 mM L-arginine. Concentrations of the antibodies were 7.75 mg/ml for GRT002-H16L2 and 4.55 mg/ml for P8C11-Chim.

Figure 5:
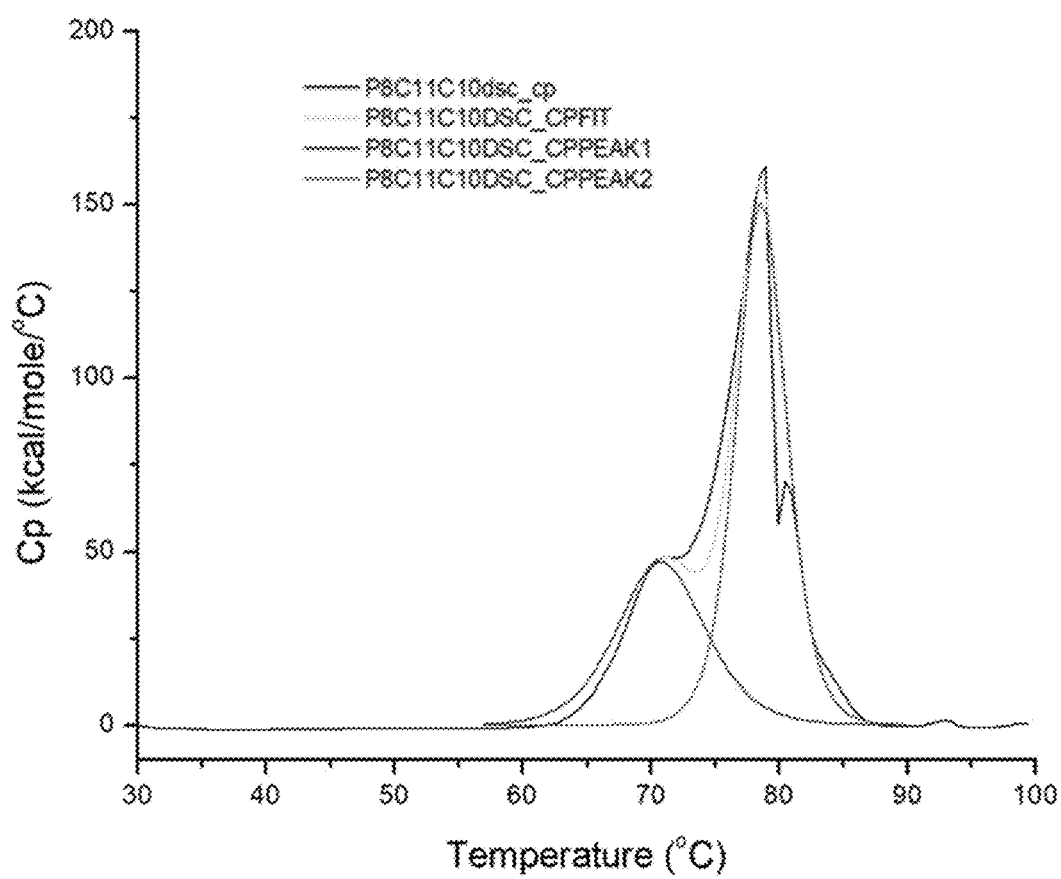
FIG. 5 shows the determination of the melting temperature of antibody P8C11 as determined by differential scanning calorimetry.
Figure 6:
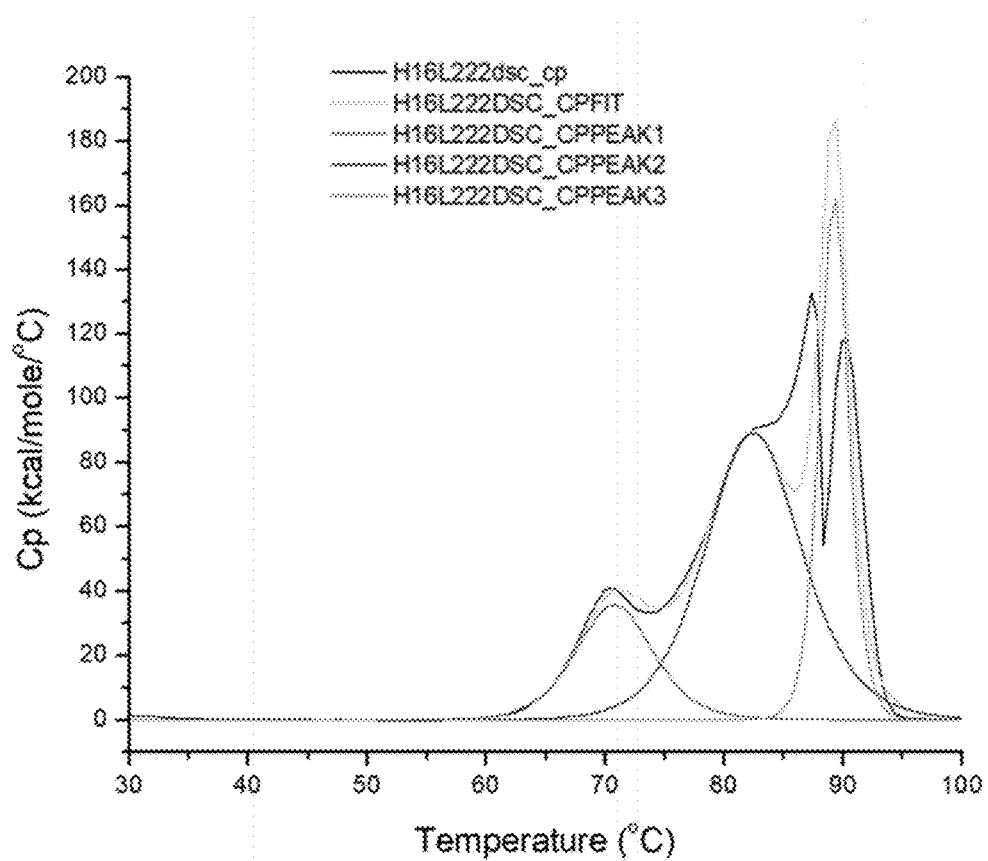
FIG. 6 shows the determination of the melting temperature of antibody GRT002-H16L2 as determined by differential scanning calorimetry.

The patterns recorded for the antibodies P8C11 and GRT002-H16L2 are shown in FIGS. 5 and 6, respectively.
Tm1=CH2 melting: 70,83° C., for P8C11-chim and 70,81° C., for GRT002-H116L2
Tm2=Fab and CH3 melting: 78,60° C., for P8C11 Chim and 82.53° C., for GRT002-H16L2.

It can be seen, that the relevant melting point Tm2 that contains the Fab region is much lower for chimeric P8C11 than for GRT002-H16L2, indicating that GRT002-H16L2 has a higher temperature stability.

Example 8.2: Freezing and Thawing

To test the behavior of the antibodies to repeated freezing and thawing, antibody GRT002-H16L2 (7.75 mg/ml in PBS mit 100 mM L-arginine) were subjected to repeated freeze-thaw cycles. After ten cycles of freezing and thawing, the samples were subjected to SEC. No effect on the integrity of the antibody could be observed in the SEC chromatogram (data not shown).

The effect of freezing and thawing was also investigated in more detail for antibody GRT002-H16L2 by way of analysing the functional activity of the antibody by measuring the level of CD131 expression in basophils. Inhibitory activity of the antibodies was measured by analyzing the ability of the antibody variants to block IL-3-induced downregulation of CD131 on primary human basophils. IL-3 (0.2 ng/ml) was preincubated for 1 h at 37° C., with various concentrations of chimeric P8C11 or GRTW02-H16L2 or PBS as control and then added to whole human EDTA blood for 1 h at 37° C. In a separate vial only PBS (no IL-3) was added to whole human EDTA blood for 1 h at 37° C., to induce no downregulation of CD131 Then the blood was stained with directly antibodies against CD123, CD203c and CD131 for 30 min on ice to identify basophils and to measure the surface level of CD131 on basophils.

Figure 7:
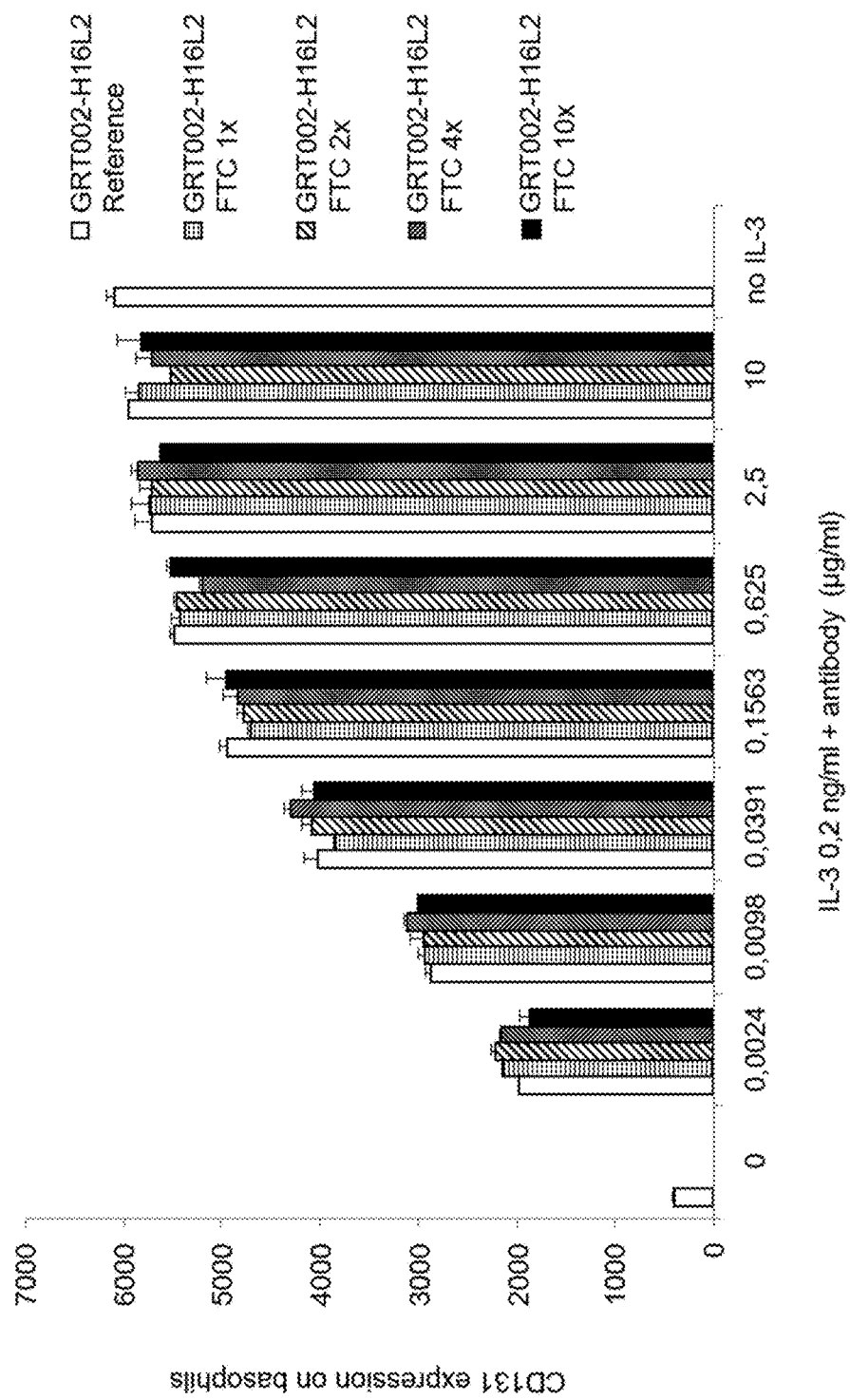
FIG. 7 shows that repeated freezing and thawing has no impact on the functional activity of GRT002-H16L2, as measured by the level of CD131 expression in basophils. FTC=freeze-thaw-cycles.

Results are shown in FIG. 7. It could be demonstrated that repeated freezing and thawing has no impact on the functional activity of GRT002-116L2.

Example 8.3: Temperature Stability

To test temperature stability of the antibodies, GRT002-H16L2 and chimeric P8C11 were investigated by analytical size-exclusion chromatography (SEC). A 7.75 mg/ml solution of GRT002-H16L2 and a 4.55 mg/ml solution of chimeric P8C11 in PBS plus 100 mM L-arginine was incubated for 3 hours at 55, 65 or 75° C., respectively, followed by analytical SEC using Superdex 200 and photometric detection of proteins at 280 nm.

The SEC pattern of both antibodies incubated at 55° C., for 3 hours was indistinguishable from the reference, i.e. the respective antibody kept at 4° C. After incubation for 3 hours at 65° C. antibody P8C11-chim showed a first shoulder at a retention volume prior to the main peak, indicating the formation of aggregates. In contrast, the SEC pattern of GRT002-H116L2 was still undistinguishable from the reference. After incubation for 3 hours at 75° C., antibody both antibodies showed a strong decrease loss of their integrity, which was however more pronounced for chimeric P8C11.

The effect of exposure to increased temperatures was also investigated for both antibodies by way of analysing the functional activity of the antibody by measuring the level of CD131 expression in basophils. The CD131 expression was analysed as described in Example 8.2.

Figure 8:
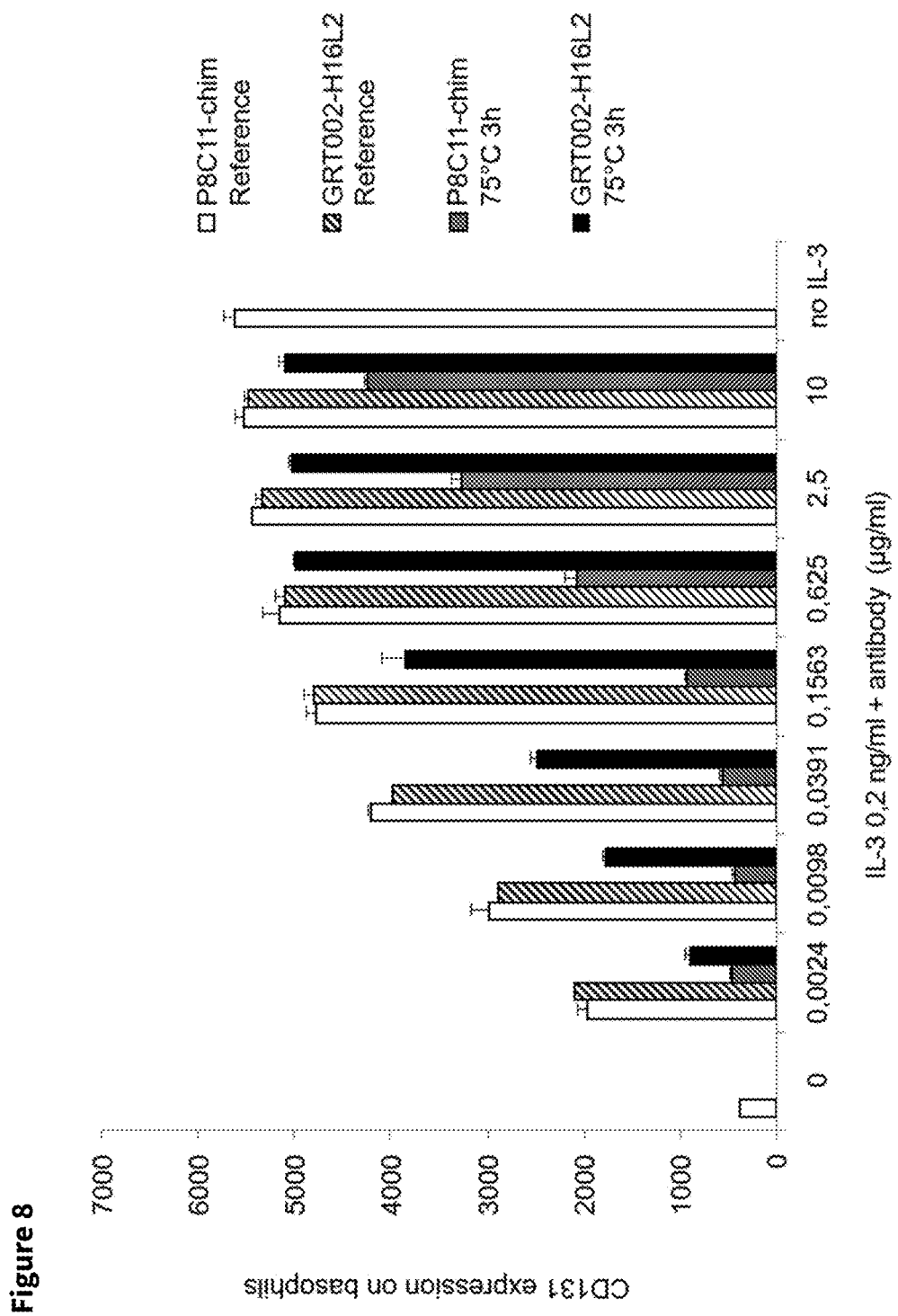
FIG. 8 shows the effect of exposure to higher temperatures of GRT002-H16L2 and chimeric P8C11 as measured by the level of CD131 expression in basophils. Antibody GRT002-H16L2 has a higher temperature stability than chimeric antibody P8C11.

Results are shown in FIG. 8 for the samples incubated for 3 hours at 75° C., compared to the reference (exposure for 3 hours at 55° C., or 65° C., did not result in any loss of the functional activity of both antibodies). It can be seen, that antibody GRT002-H16L2 shows a clearly higher functional activity after exposure for 3 hours at 75° C., as compared to the antibody P8C11-chim. At certain antibody concentrations, the functional activity of GRT002-H16L2 was more as twice as high than that of antibody P8C11-chim. After exposure to 75° C., more than 16-fold higher concentration of P8C11-chim than GRT002-H16L2 were required to obtain the same level of IL-3 inhibition.

Antibody GRT002-H16L2 has a higher temperature stability than antibody P8C11-chim.

Example 8.4: pH Stability

To test the behaviour of the antibodies, GRT002-H16L2 and chimeric P8C11 were incubated at various antibody concentrations for two hours in buffers of various pH's.

To do so, a 7.75 mg/ml solution of GRT002-H16L2 and a 4.55 mg/ml solution of chimeric P8C11 in PBS plus 100 mM L-arginine was dissolved 1:5 with water and the pH was adjusted to desired values with HC1/NaOH. Samples were then incubated at 2 hours at room temperature followed by a readjustment of the pH to 7.2 with HC1/NaOH.

The effect of exposure to different pH's was investigated for both antibodies by way of analysing the functional activity of the antibody by measuring the level of CD131 expression in basophils. The CD131 expression was analysed as described in Example 10.2.

Figure 9:
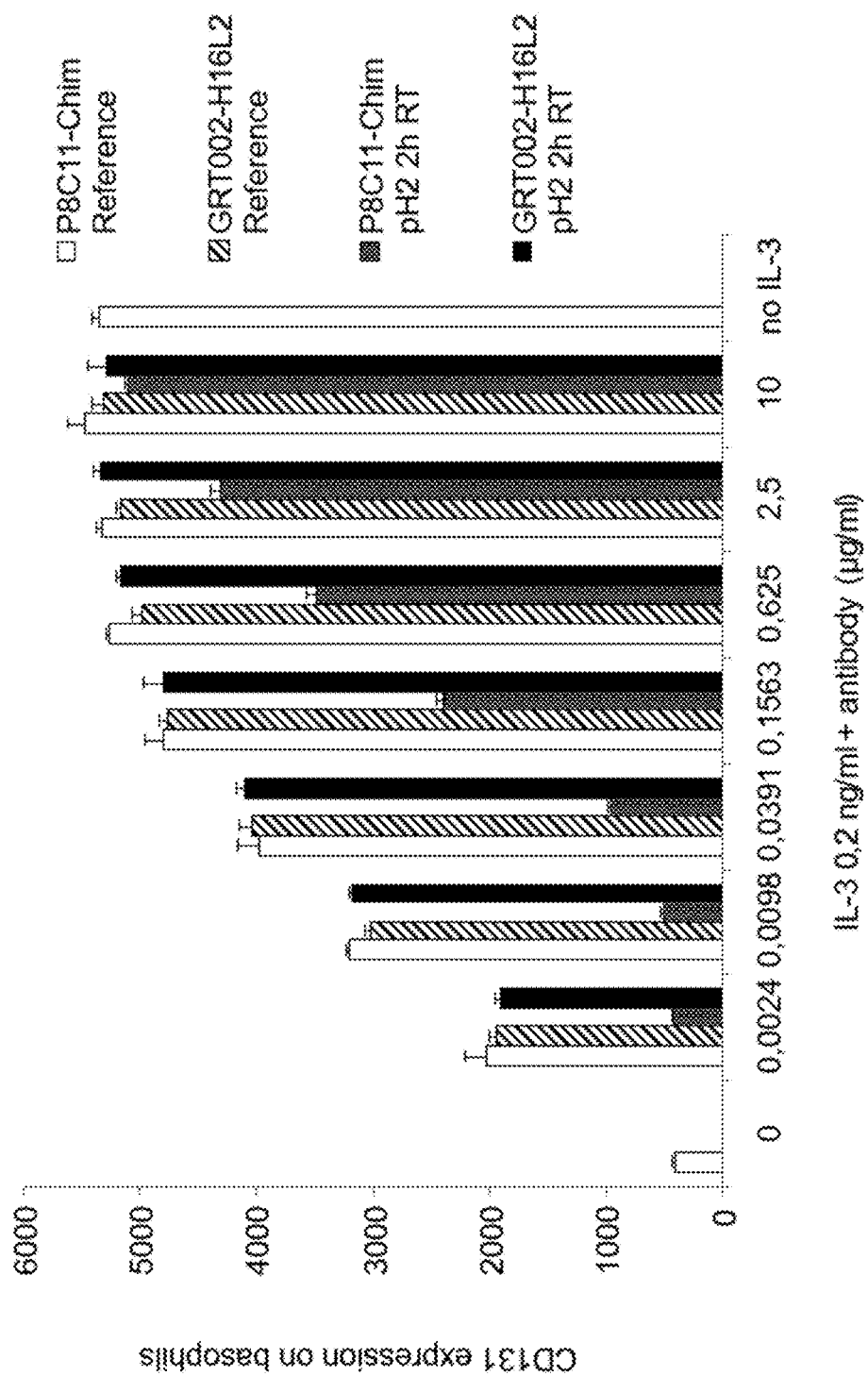
FIG. 9 shows the effect of an incubation of GRT002-H16L2 and chimeric P8C11 at a pH of 2, as measured by the level of CD131 expression in basophils. Antibody GRT002-H16L2 has a higher pH stability than antibody P8C11.

Results are shown in FIG. 9 for the samples incubated for 2 hours at a pH of 2 at room temperature to the reference (exposure for 2 hours at a pH of 3, 4, or 9 did not result in the loss of functional activity of both antibodies). It can be seen, that antibody GRT002-H16L2 fully retains its functional activity after exposure for 2 hours at a pH of 2, whereas the functional activity of antibody P8C11-chim strongly decreases. At certain antibody concentrations, the functional activity of GRT002-H16L2 was more as twice, or even three times, or four times as high than that of antibody P8C11-chim. After exposure to pH2 more than 16-fold higher concentration of P8C11-chim than GRT002-H16L2 were required to obtain the same level of IL-3 inhibition.

Antibody GRT002-H16L2 has a higher pH stability than antibody P8C11-chim.

Example 8.5: Plasma Stability

To test the long term stability of antibody GRT002-H16L2, the antibody was incubated at various concentrations for 48 hours or 14 days in PBS and human plasma.

In detail, 23.7 µl of the antibody (7.75 mg/ml in PBS with 100 mM L-arginine) was mixed with 176.3 µl PBS or human lithium-heparin plasma (1 mg/ml) and incubated for 0 hours, 48 hours or 14 days at 37° C. Thereafter, the functional activity of the antibody was determined by measuring the level of CD131 expression in basophils. The CD131 expression was analysed as described in Example 10.2.

Figure 10:
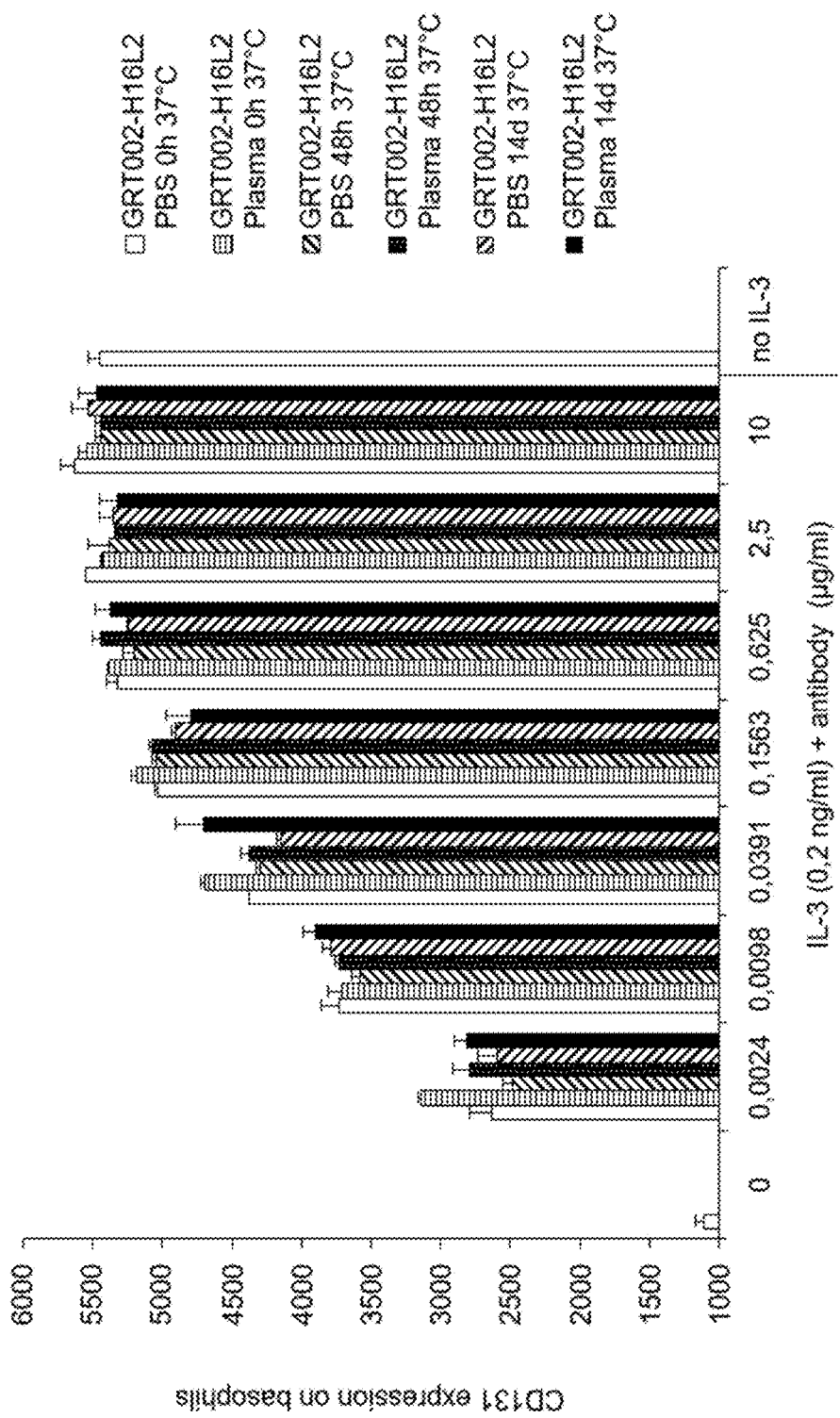
FIG. 10 shows that incubation of antibody GRT002-H16L2 for at least 14 days in human plasma has no impact on the functional activity, as measured by the level of CD131 expression in basophils.

Results are shown in FIG. 10. It could be demonstrated that antibody GRT002-H16L2 retains its fill functional activity upon incubation for at least 14 days in human plasma.

The invention claimed is:

1. An antibody or antibody fragment that specifically binds to human IL3, comprising a VH comprising HCDR1, HCDR2, and HCDR3, and a VL comprising LCDR1, LCDR2, and LCDR3, wherein the HCDR1, HCDR2, and HCDR3 comprise the HCDR1, HCDR2, and HCDR3 amino acid sequences of the VH amino acid sequence set forth in SEQ ID NO: 36; and wherein the LCDR1, LCDR2, and LCDR3 comprise the LCDR1, LCDR2, and LCDR3 of the VL amino acid sequence set forth in SEQ ID NO: 16, wherein the VH comprises the amino acid sequence set forth in SEQ ID NO: 36 and/or the VL comprises the amino acid sequence set forth in SEQ ID NO: 16.

2. The antibody or antibody fragment of claim 1, wherein the HCDR1, HCDR2, HCDR3, LCDR1, LCDR2, and LCDR3 comprise the amino acid sequences set forth in SEQ ID NO: 3, SEQ ID NO: 4, SEQ ID NO: 5, SEQ ID NO: 10, SEQ ID NO: 11, and SEQ ID NO: 12, respectively.

3. The antibody or antibody fragment of claim 2, which is an antibody of the human IgG1 class.

4. A composition comprising the antibody or antibody fragment of claim 2 and at least one pharmaceutically acceptable carrier.

5. The antibody or antibody fragment of claim 1, wherein the HCDR1, HCDR2, HCDR3, LCDR1, LCDR2, and LCDR3 comprise the amino acid sequences set forth in SEQ ID NO: 6, SEQ ID NO: 7, SEQ ID NO: 8, SEQ ID NO: 13, KAS, and SEQ ID NO: 12, respectively.

6. The humanized antibody or antibody fragment of claim 5, which is an antibody of the human IgG1 class.

7. A composition comprising the antibody or antibody fragment of claim 5 and at least one pharmaceutically acceptable carrier.

8. The antibody or antibody fragment of claim 1, wherein the VH comprises the amino acid sequence set forth in SEQ ID NO: 36.

9. The antibody or antibody fragment of claim 1, wherein the VL comprises the amino acid sequence set forth in SEQ ID NO: 16.

10. The antibody or antibody fragment of claim 1, which is an antibody of the human IgG1 class.

11. A composition comprising the antibody or antibody fragment of claim 1 and at least one pharmaceutically acceptable carrier.

12. The antibody or antibody fragment of claim 1, wherein the antibody fragment is a Fab fragment or a Fv fragment.

13. An antibody or antibody fragment that specifically binds to human IL3, comprising a VH comprising the amino acid sequence set forth in SEQ ID NO: 36, and a VL comprising the amino acid sequence set forth in SEQ ID NO: 16.

14. The antibody or antibody fragment of claim 13, which is an antibody of the human IgG1 class.

15. A composition comprising the antibody or antibody fragment of claim 13 and at least one pharmaceutically acceptable carrier.

16. The antibody or antibody fragment of claim 13, wherein the antibody fragment is a Fab fragment or a Fv fragment.

17. An antibody that specifically binds to human IL3, comprising a heavy chain comprising the amino acid sequence set forth in SEQ ID NO: 44, and a light chain comprising the amino acid sequence set forth in SEQ ID NO: 45.

18. A composition comprising the antibody of claim 17 and at least one pharmaceutically acceptable carrier.

* * * * *

```
                           SEQUENCE LISTING

Sequence total quantity: 45
SEQ ID NO: 1            moltype = AA   length = 152
FEATURE                 Location/Qualifiers
source                  1..152
                        mol_type = protein
                        organism = Homo sapiens
SEQUENCE: 1
MSRLPVLLLL QLLVRPGLQA PMTQTTPLKT SWVNCSNMID EIITHLKQPP LPLLDFNNLN   60
GEDQDILMEN NLRRPNLEAF NRAVKSLQNA SAIESILKNL LPCLPLATAA PTRHPIHIKD  120
GDWNEFRRKL TFYLKTLENA QAQQTTLSLA IF                                152

SEQ ID NO: 2            moltype = AA   length = 120
FEATURE                 Location/Qualifiers
source                  1..120
                        mol_type = protein
                        organism = synthetic construct
SEQUENCE: 2
QVQLQQSGAE MVRPGVSVKI ACKGSGFTFT DYALHWVKQS HAKSLEWIGL ISTYYGDTTY   60
NQRFKGKATM TVDKSSSTAY MELARLTSED SAIYYCVITT VAGTDAMDYW GQGTSVTVSS  120

SEQ ID NO: 3            moltype = AA   length = 5
FEATURE                 Location/Qualifiers
source                  1..5
                        mol_type = protein
                        organism = synthetic construct
SEQUENCE: 3
DYALH                                                                5

SEQ ID NO: 4            moltype = AA   length = 17
FEATURE                 Location/Qualifiers
source                  1..17
                        mol_type = protein
                        organism = synthetic construct
SEQUENCE: 4
LISTYYGDTT YNQRFKG                                                  17

SEQ ID NO: 5            moltype = AA   length = 11
FEATURE                 Location/Qualifiers
source                  1..11
                        mol_type = protein
                        organism = synthetic construct
SEQUENCE: 5
TTVAGTDAMD Y                                                        11

SEQ ID NO: 6            moltype = AA   length = 8
FEATURE                 Location/Qualifiers
source                  1..8
                        mol_type = protein
                        organism = synthetic construct
SEQUENCE: 6
GFTFTDYA                                                             8

SEQ ID NO: 7            moltype = AA   length = 8
FEATURE                 Location/Qualifiers
source                  1..8
                        mol_type = protein
                        organism = synthetic construct
SEQUENCE: 7
ISTYYGDT                                                             8

SEQ ID NO: 8            moltype = AA   length = 13
FEATURE                 Location/Qualifiers
source                  1..13
                        mol_type = protein
                        organism = synthetic construct
SEQUENCE: 8
VITTVAGTDA MDY                                                      13

SEQ ID NO: 9            moltype = AA   length = 107
FEATURE                 Location/Qualifiers
```

```
                        source             1..107
                                           mol_type = protein
                                           organism = synthetic construct
SEQUENCE: 9
DIQMNQSPSS LSASLGDTIT ITCHASQNIN VWLSWYQQKP GNIPKLLIYK ASNLHTGVPS      60
RFSGSGSGTG FTLTISSLQP EDIATYYCQQ GYSYPYTFGG GTKLEIK                   107

SEQ ID NO: 10           moltype = AA  length = 11
FEATURE                 Location/Qualifiers
source                  1..11
                        mol_type = protein
                        organism = synthetic construct
SEQUENCE: 10
HASQNINVWL S                                                           11

SEQ ID NO: 11           moltype = AA  length = 7
FEATURE                 Location/Qualifiers
source                  1..7
                        mol_type = protein
                        organism = synthetic construct
SEQUENCE: 11
KASNLHT                                                                7

SEQ ID NO: 12           moltype = AA  length = 9
FEATURE                 Location/Qualifiers
source                  1..9
                        mol_type = protein
                        organism = synthetic construct
SEQUENCE: 12
QQGYSYPYT                                                              9

SEQ ID NO: 13           moltype = AA  length = 6
FEATURE                 Location/Qualifiers
source                  1..6
                        mol_type = protein
                        organism = synthetic construct
SEQUENCE: 13
QNINVW                                                                 6

SEQ ID NO: 14           moltype =     length =
SEQUENCE: 14
000

SEQ ID NO: 15           moltype = AA  length = 107
FEATURE                 Location/Qualifiers
source                  1..107
                        mol_type = protein
                        organism = Homo sapiens
SEQUENCE: 15
DIQMTQSPSS VSASVGDRVT ITCHASQNIN VWLSWYQQKP GKAPKLLIYK ASNLHTGVPS      60
RFSGSGSGTD FTLTISSLQP EDFATYYCQQ GYSYPYTFGG GTKLEIK                   107

SEQ ID NO: 16           moltype = AA  length = 107
FEATURE                 Location/Qualifiers
source                  1..107
                        mol_type = protein
                        organism = Homo sapiens
SEQUENCE: 16
DIQMTQSPSS LSASVGDRVT ITCHASQNIN VWLSWYQQKP GKAPKLLIYK ASNLHTGVPS      60
RFSGSGSGTD FTFTISSLQP EDIATYYCQQ GYSYPYTFGG GTKLEIK                   107

SEQ ID NO: 17           moltype = AA  length = 107
FEATURE                 Location/Qualifiers
source                  1..107
                        mol_type = protein
                        organism = Homo sapiens
SEQUENCE: 17
DIQMTQSPSS LSASVGDRVT ITCHASQNIN VWLSWYQQKP GKVPKLLIYK ASNLHTGVPS      60
RFSGSGSGTD FTLTISSLQP EDVATYYCQQ GYSYPYTFGG GTKLEIK                   107

SEQ ID NO: 18           moltype = AA  length = 120
FEATURE                 Location/Qualifiers
source                  1..120
                        mol_type = protein
                        organism = Homo sapiens
SEQUENCE: 18
QVQLVQSGAE VKKPGASVKV SCKASGFTFT DYALHWVRQA PGQRLEWMGL ISTYYGDTTY      60
NQRFKGRVTI TRDTSASTAY MELSSLRSED TAVYYCVITT VAGTDAMDYW GQGTLVTVSS    120
```

```
SEQ ID NO: 19              moltype = AA   length = 120
FEATURE                    Location/Qualifiers
source                     1..120
                           mol_type = protein
                           organism = Homo sapiens
SEQUENCE: 19
QVQLVQSGSE LKKPGASVKV SCKASGFTFT DYALHWVRQA PGQGLEWMGL ISTYYGDTTY    60
NQRFKGRFVF SLDTSVSTAY LQISSLKAED TAVYYCVITT VAGTDAMDYW GQGTLVTVSS   120

SEQ ID NO: 20              moltype = AA   length = 120
FEATURE                    Location/Qualifiers
source                     1..120
                           mol_type = protein
                           organism = synthetic construct
SEQUENCE: 20
QVQLVQSGAE MKKPGASVKV ACKGSGFTFT DYALHWVRQA PGQRLEWMGL ISTYYGDTTY    60
NQRFKGRVTI TRDTSASTAY MELSSLRSED TAIYYCVITT VAGTDAMDYW GQGTLVTVSS   120

SEQ ID NO: 21              moltype = AA   length = 120
FEATURE                    Location/Qualifiers
source                     1..120
                           mol_type = protein
                           organism = synthetic construct
SEQUENCE: 21
QVQLQQSGAE MVRPGVSVKI ACKGSGFTFT DYALHWVKQS HAKSLEWIGL ISTYYGDTTY    60
NQRFKGRVTI TRDTSASTAY MELSSLRSED TAIYYCVITT VAGTDAMDYW GQGTLVTVSS   120

SEQ ID NO: 22              moltype = AA   length = 120
FEATURE                    Location/Qualifiers
source                     1..120
                           mol_type = protein
                           organism = synthetic construct
SEQUENCE: 22
QVQLQQSGAE MVRPGVSVKI ACKGSGFTFT DYALHWVRQA PGQRLEWMGL ISTYYGDTTY    60
NQRFKGKATM TVDKSSSTAY MELARLTSED SAIYYCVITT VAGTDAMDYW GQGTSVTVSS   120

SEQ ID NO: 23              moltype = AA   length = 120
FEATURE                    Location/Qualifiers
source                     1..120
                           mol_type = protein
                           organism = synthetic construct
SEQUENCE: 23
QVQLVQSGAE MKKPGASVKV ACKGSGFTFT DYALHWVKQS HAKSLEWIGL ISTYYGDTTY    60
NQRFKGKATM TVDKSSSTAY MELARLTSED SAIYYCVITT VAGTDAMDYW GQGTSVTVSS   120

SEQ ID NO: 24              moltype = AA   length = 120
FEATURE                    Location/Qualifiers
source                     1..120
                           mol_type = protein
                           organism = synthetic construct
SEQUENCE: 24
QVQLVQSGAE MKKPGASVKV ACKGSGFTFT DYALHWVRQA PGQRLEWMGL ISTYYGDTTY    60
NQRFKGKATM TVDKSSSTAY MELSSLRSED TAIYYCVITT VAGTDAMDYW GQGTLVTVSS   120

SEQ ID NO: 25              moltype = AA   length = 120
FEATURE                    Location/Qualifiers
source                     1..120
                           mol_type = protein
                           organism = synthetic construct
SEQUENCE: 25
QVQLVQSGAE MKKPGASVKV ACKGSGFTFT DYALHWVRQA PGQRLEWMGL ISTYYGDTTY    60
NQRFKGRVTI TRDTSASTAY MELARLTSED SAIYYCVITT VAGTDAMDYW GQGTSVTVSS   120

SEQ ID NO: 26              moltype = AA   length = 120
FEATURE                    Location/Qualifiers
source                     1..120
                           mol_type = protein
                           organism = synthetic construct
SEQUENCE: 26
QVQLVQSGAE MKKPGASVKV ACKGSGFTFT DYALHWVRQA PGQRLEWMGL ISTYYGDTTY    60
NQRFKGRVTM TVDKSSSTAY MELSSLRSED TAIYYCVITT VAGTDAMDYW GQGTLVTVSS   120

SEQ ID NO: 27              moltype = AA   length = 120
FEATURE                    Location/Qualifiers
source                     1..120
                           mol_type = protein
                           organism = synthetic construct
```

```
SEQUENCE: 27
QVQLVQSGAE VKKPGASVKV ACKGSGFTFT DYALHWVRQA PGQRLEWMGL ISTYYGDTTY    60
NQRFKGRVTM TVDKSSSTAY MELSSLRSED TAVYYCVITT VAGTDAMDYW GQGTLVTVSS   120

SEQ ID NO: 28           moltype = AA   length = 120
FEATURE                 Location/Qualifiers
source                  1..120
                        mol_type = protein
                        organism = synthetic construct
SEQUENCE: 28
QVQLVQSGAE MKKPGASVKV SCKASGFTFT DYALHWVRQA PGQRLEWMGL ISTYYGDTTY    60
NQRFKGRVTM TVDKSSSTAY MELSSLRSED TAIYYCVITT VAGTDAMDYW GQGTLVTVSS   120

SEQ ID NO: 29           moltype = AA   length = 120
FEATURE                 Location/Qualifiers
source                  1..120
                        mol_type = protein
                        organism = synthetic construct
SEQUENCE: 29
QVQLVQSGAE MKKPGASVKV ACKGSGFTFT DYALHWVRQA PGQRLEWMGL ISTYYGDTTY    60
NQRFKGRVTM TVDKSASTAY MELSSLRSED TAIYYCVITT VAGTDAMDYW GQGTLVTVSS   120

SEQ ID NO: 30           moltype = AA   length = 120
FEATURE                 Location/Qualifiers
source                  1..120
                        mol_type = protein
                        organism = synthetic construct
SEQUENCE: 30
QVQLVQSGAE MKKPGASVKV ACKGSGFTFT DYALHWVRQA PGQRLEWMGL ISTYYGDTTY    60
NQRFKGRVTI TVDKSASTAY MELSSLRSED TAIYYCVITT VAGTDAMDYW GQGTLVTVSS   120

SEQ ID NO: 31           moltype = AA   length = 120
FEATURE                 Location/Qualifiers
source                  1..120
                        mol_type = protein
                        organism = synthetic construct
SEQUENCE: 31
QVQLVQSGAE VKKPGASVKV ACKGSGFTFT DYALHWVRQA PGQRLEWMGL ISTYYGDTTY    60
NQRFKGRVTM TADKSTSTAY MELSSLRSED TAVYYCVITT VAGTDAMDYW GQGTLVTVSS   120

SEQ ID NO: 32           moltype = AA   length = 120
FEATURE                 Location/Qualifiers
source                  1..120
                        mol_type = protein
                        organism = synthetic construct
SEQUENCE: 32
QVQLVQSGAE VKKPGASVKV ACKGSGFTFT DYALHWVRQA PGQRLEWMGL ISTYYGDTTY    60
NQRFKGRVTM TVDKSTSTAY MELSSLRSED TAVYYCVITT VAGTDAMDYW GQGTLVTVSS   120

SEQ ID NO: 33           moltype = AA   length = 120
FEATURE                 Location/Qualifiers
source                  1..120
                        mol_type = protein
                        organism = synthetic construct
SEQUENCE: 33
QVQLVQSGAE VKKPGASVKV ACKGSGFTFT DYALHWVRQA PGQRLEWMGL ISTYYGDTTY    60
NQRFKGRVTM TADKSSSTAY MELSSLRSED TAVYYCVITT VAGTDAMDYW GQGTLVTVSS   120

SEQ ID NO: 34           moltype = AA   length = 120
FEATURE                 Location/Qualifiers
source                  1..120
                        mol_type = protein
                        organism = synthetic construct
SEQUENCE: 34
QVQLVQSGAE VKKPGASVKV SCKGSGFTFT DYALHWVRQA PGQRLEWMGL ISTYYGDTTY    60
NQRFKGRVTM TADKSTSTAY MELSSLRSED TAVYYCVITT VAGTDAMDYW GQGTLVTVSS   120

SEQ ID NO: 35           moltype = AA   length = 120
FEATURE                 Location/Qualifiers
source                  1..120
                        mol_type = protein
                        organism = synthetic construct
SEQUENCE: 35
QVQLVQSGAE VKKPGASVKV ACKASGFTFT DYALHWVRQA PGQRLEWMGL ISTYYGDTTY    60
NQRFKGRVTM TADKSTSTAY MELSSLRSED TAVYYCVITT VAGTDAMDYW GQGTLVTVSS   120

SEQ ID NO: 36           moltype = AA   length = 120
FEATURE                 Location/Qualifiers
```

```
source                  1..120
                        mol_type = protein
                        organism = synthetic construct
SEQUENCE: 36
QVQLVQSGAE VKKPGASVKV SCKGSGFTFT DYALHWVRQA PGQRLEWMGL ISTYYGDTTY    60
NQRFKGRVTM TVDKSTSTAY MELSSLRSED TAVYYCVITT VAGTDAMDYW GQGTLVTVSS   120

SEQ ID NO: 37           moltype = AA  length = 27
FEATURE                 Location/Qualifiers
source                  1..27
                        mol_type = protein
                        organism = Homo sapiens
SEQUENCE: 37
EIITHLKQPP LPLLDFNNLN GEDQDIL                                        27

SEQ ID NO: 38           moltype = AA  length = 23
FEATURE                 Location/Qualifiers
source                  1..23
                        mol_type = protein
                        organism = Homo sapiens
SEQUENCE: 38
HLKQPPLPLL DFNNLNGEDQ DIL                                            23

SEQ ID NO: 39           moltype = AA  length = 21
FEATURE                 Location/Qualifiers
source                  1..21
                        mol_type = protein
                        organism = Homo sapiens
SEQUENCE: 39
KQPPLPLLDF NNLNGEDQDI L                                              21

SEQ ID NO: 40           moltype = AA  length = 19
FEATURE                 Location/Qualifiers
source                  1..19
                        mol_type = protein
                        organism = Homo sapiens
SEQUENCE: 40
PPLPLLDFNN LNGEDQDIL                                                 19

SEQ ID NO: 41           moltype = AA  length = 21
FEATURE                 Location/Qualifiers
source                  1..21
                        mol_type = protein
                        organism = Homo sapiens
SEQUENCE: 41
EIITHLKQPP LPLLDFNNLN G                                              21

SEQ ID NO: 42           moltype = AA  length = 23
FEATURE                 Location/Qualifiers
source                  1..23
                        mol_type = protein
                        organism = Homo sapiens
SEQUENCE: 42
EIITHLKQPP LPLLDFNNLN GED                                            23

SEQ ID NO: 43           moltype = AA  length = 25
FEATURE                 Location/Qualifiers
source                  1..25
                        mol_type = protein
                        organism = Homo sapiens
SEQUENCE: 43
EIITHLKQPP LPLLDFNNLN GEDQD                                          25

SEQ ID NO: 44           moltype = AA  length = 449
FEATURE                 Location/Qualifiers
source                  1..449
                        mol_type = protein
                        organism = synthetic construct
SEQUENCE: 44
QVQLVQSGAE VKKPGASVKV SCKGSGFTFT DYALHWVRQA PGQRLEWMGL ISTYYGDTTY    60
NQRFKGRVTM TVDKSTSTAY MELSSLRSED TAVYYCVITT VAGTDAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKRVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPG                                    449

SEQ ID NO: 45           moltype = AA  length = 214
```

```
FEATURE                 Location/Qualifiers
source                  1..214
                        mol_type = protein
                        organism = synthetic construct
SEQUENCE: 45
DIQMTQSPSS LSASVGDRVT ITCHASQNIN VWLSWYQQKP GKAPKLLIYK ASNLHTGVPS   60
RFSGSGSGTD FTFTISSLQP EDIATYYCQQ GYSYPYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```